United States Patent [19]

Fujita et al.

[11] 4,179,579

[45] Dec. 18, 1979

[54] SUBSTITUTED PROPARGYL ALCOHOLS, ALLYLIC ALCOHOLS AND UNSATURATED KETONES, AND METHODS FOR THE PRODUCTION THEREOF

[75] Inventors: Yoshiji Fujita; Fumio Wada; Takashi Ohnishi; Takashi Nishida, all of Kurashiki; Yoshiaki Omura, Mitsu; Fumio Mori, Kurashiki; Takeo Hosogai, Kurashiki; Sukeji Aihara, Kurashiki, all of Japan

[73] Assignee: Kuraray Co., Ltd., Kurashiki, Japan

[21] Appl. No.: 818,875

[22] Filed: Jul. 25, 1977

Related U.S. Application Data

[63] Continuation-in-part of Ser. No. 746,738, Dec. 2, 1976, abandoned.

[30] Foreign Application Priority Data

| Dec. 2, 1975 | [JP] | Japan | 50-144267 |
|---|---|---|---|
| Dec. 2, 1975 | [JP] | Japan | 50-144268 |
| Dec. 30, 1975 | [JP] | Japan | 50-159584 |
| Feb. 16, 1976 | [JP] | Japan | 51-16611 |

[51] Int. Cl.$^2$ ............ C07C 33/02; C07C 33/04
[52] U.S. Cl. ............... 568/840; 260/593 R; 260/594; 568/875; 568/873; 568/857; 568/596; 568/597; 568/674; 568/675; 568/878; 568/841; 568/874
[58] Field of Search .............. 260/832 R, 832 Y; 568/873, 875, 840, 857

[56] References Cited

U.S. PATENT DOCUMENTS

| 2,799,706 | 7/1957 | Kimel et al. | 260/586 |
|---|---|---|---|
| 2,841,620 | 7/1958 | Colaanni et al. | 260/632 R |
| 3,082,260 | 3/1963 | Tedeschi et al. | 260/632 Y |
| 3,296,080 | 1/1967 | Meuly et al. | 260/632 R |
| 3,379,777 | 4/1968 | Riehen | 260/632 Y |
| 3,549,714 | 12/1970 | Marbit | 260/632 Y |
| 3,573,299 | 3/1971 | Andrews et al. | 260/632 Y |
| 3,716,565 | 2/1973 | Henrick et al. | 260/632 Y |
| 3,886,215 | 5/1975 | Desimone et al. | 260/632 Y |

*Primary Examiner*—James H. Reamer
*Attorney, Agent, or Firm*—Burns, Doane, Swecker & Mathis

[57] ABSTRACT

Novel substituted propargyl alcohols of the formula:

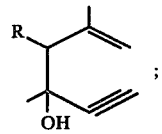

novel allylic alcohols of the formula:

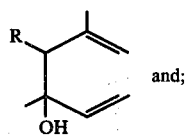

and;

$\delta,\epsilon$-unsaturated ketones of the formula:

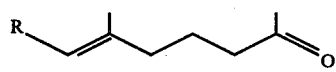

are provided.

In the above formulas, R represents a group of the formula:

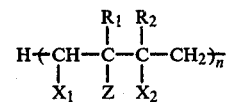

wherein $X_1$ and $X_2$ are both hydrogen atoms or wherein one of $X_1$ and $X_2$ is a hydrogen atom, the other jointly with Z represents a bond; Z jointly with $X_1$ or $X_2$ represents a bond or separately represent a hydrogen atom, a hydroxyl group or a lower alkoxy group; $R_1$ and $R_2$ are the same or different and represents hydrogen atoms or lower alkyl groups; n is 1 or 2; and when n is 2, $X_1$, $X_2$, X, $R_1$ and $R_2$ may be the same or different. These novel compounds are easily produced and are useful as perfumes and as interrelated intermediates for the production of terpenoid compounds.

29 Claims, No Drawings

SUBSTITUTED PROPARGYL ALCOHOLS, ALLYLIC ALCOHOLS AND UNSATURATED KETONES, AND METHODS FOR THE PRODUCTION THEREOF

CROSS REFERENCE TO RELATED APPLICATION

This application is a continuation-in-part of Ser. No. 746,738, filed Dec. 2, 1976 now abandoned.

BACKGROUND OF THE INVENTION

1. Field of the Invention

The present invention relates to novel substituted propargyl alcohols, novel allylic alcohols corresponding to said propargyl alcohols and novel unsaturated ketones which are structural isomers of said allylic alcohols, and the methods of production of such compounds. In still another aspect, this invention relates to novel unsaturated terpene ketones, their intermediate compounds and the production thereof.

2. Description of the Prior Art

A typical process known for the production of terpenoid compounds involves a multiple-step procedure based on the Carroll rearrangement using diketene which is a prevalent C3 chain extender or the Claisen rearrangement involving the use of isopropenyl ether. For example, the steps for the poduction of geranyl acetone starting with methyl heptenone may be illustrated as ofllows [See, e.g., J. Chem. Soc. 704 and 1266 (1940) and 570 (1941), Angewandte Chemie 72, 869 (1960), U.S. Pat. Nos. 2,795,617, 2,628,250, and 3,049,565]:

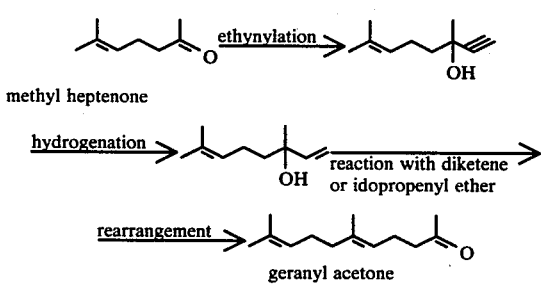

The chain extenders diketene and isopropentyl ether are comparatively expensive and the additional step for such a chain-extending reaction is unavoidable. In contrast, the use of the novel substituted propargyl alcohols and novel allylic alcohols of this invention are easily obtainable from inexpensive materials without the use of C3 chain extenders such as diketene and isopropenyl ether, and provide for the production of the desired terpenoid compounds in a more efficient and economical method.

SUMMARY OF THE INVENTION

The substituted propargyl alcohols according to this invention are represented by the following general formula (III):

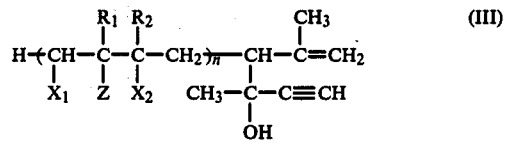

In the formula (III), $X_1$ and $X_2$ are both hydrogen atoms or one of $X_1$ and $X_2$ is a hydrogen atom, the other jointly with Z represents a bond; Z represents a bond jointly with $X_1$ or $X_2$ or separately is a hydrogen atom, a hydroxyl group or a lower alkoxy group; $R_1$ and $R_2$ are the same or different and are hydrogen atoms or lower alkyl groups; n is 1 or 2; and when n is 2, $X_1$, $X_2$, Z, $R_1$ and $R_2$ may be the same or different.

The allylic alcohols according to this invention are represented by the following formula (II):

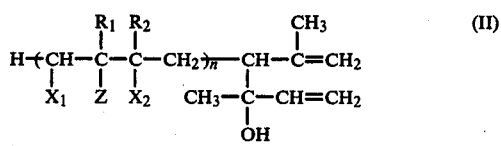

In the formula (II), $X_1$, $X_2$, Z, $R_1$, $R_2$ and n are the same as defined for the formula (III).

The unsaturated ketones produced from the allylic alcohols of formula (II) according to this invention are δ,ε-unsaturated ketones of the following general formula (I) which are structural isomers of said allylic alcohols.

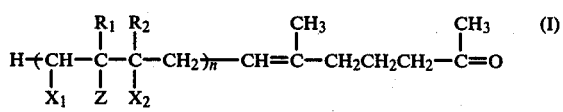

In the formula (I), $X_1$, $X_2$, Z, $R_1$, $R_2$ and n have the same meanings as respectively defined in connection with the formula (III).

The substituted propargyl alcohols of formula (III), the substituted allylic alcohols of formula (II), and the δ,ε-unsaturated ketones of formula (I) are perfumes, per se, and are intermediates for the production of other perfumery products, cosmetic bases, pharmaceuticals, agricultural chemicals and similar uses.

Accordingly, it is an object of this invention to provide novel substituted propargyl alcohols, substituted allylic alcohols and δ,ε-unsaturated ketones.

Another object of this invention is to provide an economical and efficient method for the production of substituted propargyl alcohols, substituted allylic alcohols and δ,ε-unsaturated ketones.

A further object of this invention is to provide a commercial route to the production of substituted propargyl alcohols, substituted allylic alcohols and δ,ε-unsaturated ketones.

A still further object of this invention is to provide an economical and efficient method for the production of terpenoid compounds.

A particular object of this invention is to provide methods for preparing the novel compounds as represented by formulas I, II and III, which use readily available starting materials.

Still other objects of this invention will be apparent from the specification.

DESCRIPTION OF THE PREFERRED EMBODIMENTS

The following detailed description will assist in a better understanding of this invention.

A. Substituted Propargyl Alcohols and Methods for the Production of Same

The peculiar structure of the substituted propargyl alcohol according to this invention is derived from the mesityl oxide, i.e., 4-methyl-3-penten-2-one;

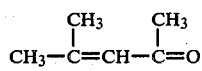

and/or isomesityl oxide, i.e. 4-methyl-4-penten-2-one;

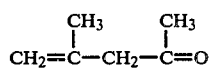

As illustrated below, the substituted propargyl alcohol is produced by a first step of reacting a halide of said group R with mesityl oxide and/or isomesityl oxide to obtain an α,β-unsaturated ketone of the following formula (V) and/or a β,γ-unsaturated ketone of the following formula (IV) and a second step of ethynylating said ketone or ketones.

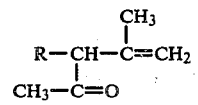
(IV)

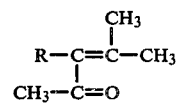
(V)

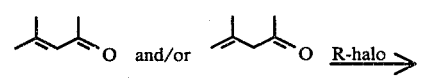

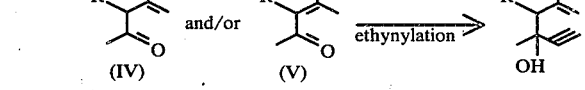

In the above formulas and equations, halo. means a halogen atom and R is defined by the following structural formula:

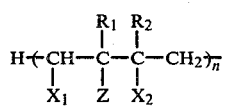

wherein Z is a lower alkoxy group, and preferably methoxy, ethoxy, propoxy or butoxy. Where $R_1$ and $R_2$ are both lower alkyl groups, reference may be made to alkyl groups of 1 to 5 carbon atoms, such as methyl, ethyl, n-propyl, isopropyl, n-butyl, t-butyl, n-amyl, isoamyl, etc. As preferred examples of R may be mentioned the following:

| Nomenclature of group R | Chemical formula |
|---|---|
| n-Butyl | $CH_3CH_2CH_2CH_2—$ |
| Isoamyl | $CH_3—\underset{\underset{CH_3}{\|}}{CH}—CH_2CH_2—$ |
| Prenyl | $CH_3—\underset{\underset{CH_3}{\|}}{C}=CH—CH_2—$ |
| 3-Methyl-3-butenyl | $CH_2=\underset{\underset{CH_3}{\|}}{C}—CH_2—CH_2—$ |
| 2,3-Dimethyl-3-hydroxy-butyl | $CH_3—\underset{\underset{OH}{\|}}{C}—\underset{\underset{CH_3}{\|}}{CH}—CH_2—$ |
| 3-Methyl-2-pentenyl | $CH_3—\underset{\underset{C_2H_5}{\|}}{C}=CH—CH_2—$ |
| 2,3-Dimethyl-2-butenyl | $CH_3—\underset{\underset{CH_3}{\|}}{C}=\underset{\underset{CH_3}{\|}}{C}—CH_2—$ |
| 2,3-Dimethyl-2-pentenyl | $CH_3—\underset{\underset{C_2H_5}{\|}}{C}=\underset{\underset{CH_3}{\|}}{C}—CH_2—$ |
| 2-Ethyl-3-methyl-2-butenyl | $CH_3—\underset{\underset{CH_3}{\|}}{C}=\underset{\underset{C_2H_5}{\|}}{C}—CH_2—$ |
| 2,3-dimethyl-3-methoxybutyl | $CH_3—\underset{\underset{OCH_3}{\|}}{\overset{\overset{CH_3}{\|}}{C}}—\underset{\underset{CH_3}{\|}}{CH}—CH_2—$ |
| 3,7-Dimethyl-octyl | $CH_3—\underset{\underset{CH_3}{\|}}{CH}—(CH_2)_3—\underset{\underset{CH_3}{\|}}{CH}—CH_2CH_2—$ |
| 3,7-Dimethyl-2,6-octadienyl | $CH_3—\underset{\underset{CH_3}{\|}}{C}=CH—(CH_2)_2—\underset{\underset{CH_3}{\|}}{C}=CH—CH_2—$ |
| 3,7-Dimethyl-2,7-octadienyl | $CH_2=\underset{\underset{CH_3}{\|}}{C}—CH_2CH_2CH_2—\underset{\underset{CH_3}{\|}}{C}=CH—CH_2—$ |
| 3,7-Dimethyl-6-octenyl | $CH_3—\underset{\underset{CH_3}{\|}}{C}=CH—(CH_2)_2—\underset{\underset{CH_3}{\|}}{CH}—CH_2—CH_2—$ |
| 3,7-Dimethyl-2-octenyl | $CH_3—\underset{\underset{CH_3}{\|}}{CH}—(CH_2)_3—\underset{\underset{CH_3}{\|}}{C}=CH—CH_2—$ |
| 7-Methyl-3-ethyl-2,6-nonadienyl | $CH_3—\underset{\underset{C_2H_5}{\|}}{C}=CH—(CH_2)_2—\underset{\underset{C_2H_5}{\|}}{C}=CH—CH_2—$ |
| 3,7-Dimethyl-7-hydroxy-octyl | $CH_3—\underset{\underset{OH}{\|}}{\overset{\overset{CH_3}{\|}}{C}}—(CH_2)_3—\underset{\underset{CH_3}{\|}}{CH}—CH_2—CH_2—$ |
| 3,7-Dimethyl-7-methoxy-octyl | $CH_3—\underset{\underset{OCH_3}{\|}}{\overset{\overset{CH_3}{\|}}{C}}—(CH_2)_3—\underset{\underset{CH_3}{\|}}{CH}—CH_2CH_2—$ |

1. Production of the α,β-unsaturated ketone and the β,γ-unsaturated ketone

The production of the α,β-unsaturated and β,γ-unsaturated ketones which are employed in the production of the substituted propargyl alcohols of this invention does not constitute an essential part of the invention, the ketones are prepared by known procedures. For reference sake, the production processes for these ketones will be described below.

Mesityl oxide and isomesityl oxide have been commercially produced by the dehydration of diacetone alcohol which is a dimer of acetone. Depending upon the reaction conditions, from 5 to 20 percent of the formed mixture of 4-methylpenten-2-ones is 4-methyl-4-penten-2-one (isomesityl oxide) and the balance is 4-methyl-3-penten-2-one (mesityl oxide). Since mesityl oxide and isomesityl oxide are separable by distillation they may be used singly or together in the reaction with the organic halide R-halo. However, it is preferable to use mixtures of mesityl oxide and isomesityl oxide. The general reaction of ketones with organic halides to yield substituted ketones is known. It is also known that, as a preferred procedure, the reaction is conducted in the presence of an alkaline condensing agent, such as sodium hydroxide and potassium hydroxide in the presence of an amine compound, tertiary ammonium salt or phosphonium compound as a catalyst, (British Pat. Nos. 851,658 and 1,059,839 and U.S. Pat. No. 3,668,255).

In the present invention, the reaction of the organic halide with mesityl oxide and/or isomesityl oxide is conducted in a conventional manner and if either mesityl or isomesityl oxides is employed singly, the reaction mixture generally yields both a $\beta,\gamma$-unsaturated ketone of formula (IV) and an $\alpha,\beta$-unsaturated ketone of formula (V) as products. In the above reaction, the alkaline condensing agent is used in an amount from about 1 to about 10 mole equivalents, preferably within the range of about 1.5 to 4 moles, based on the organic halide R-halo. The alkaline condensing agent is added to the reaction system, either as is or in the form of an aqueous solution containing about 40 to 65 weight percent of said agent. The catalyst may be a primary amine secondary amine or tertiary amine, a salt of such an amine, a quaternary ammonium salt or a phosphonium salt, preferred species including tetrabutylammonium chloride, trimethylbenzylammonium chloride, trimethyllaurylammonium chloride, trimethylcetylammonium chloride, trimethylstearylammonium chloride, trimethylstearylammonium bromide, dimethyldicyclohexylphosphonium chloride, methyltricyclohexylphosphonium chloride, ethyltricyclohexylphosphonium chloride and ethyltricyclohexylphosphonium bromide. The preferred amount of said catalyst is generally in the range of about 0.001 to 20 mole percent and, preferably about 0.005 to 2.0 mole percent based on the organic halide. The reaction temperature is in the range of 0° to 100° C. The range of about 20° to 70° C. is particularly preferred. Under the reaction conditions described above, the reaction goes to completion in about 1 to 30 hours. To obtain a higher ratio of $\beta,\gamma$-unsaturated ketone (IV) to $\alpha,\beta$-unsaturated ketone (V) in connection with the above reaction, the reaction must be terminated when the conversion of the organic halide has reached about 70 to 80 percent. This higher ratio of $\beta,\gamma$- to a $\alpha,\beta$- is preferred since it is usually difficult to produce the corresponding propargyl alcohol of the following formula (III') through the ethynylation of an $\alpha,\beta$-unsaturated ketone of formula (V).

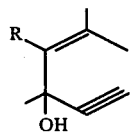

(III')

wherein R is as defined hereinbefore.

The difference in boiling point between the $\alpha,\beta$-unsaturated ketone and the $\beta,\gamma$-unsaturated ketone allows the $\alpha,\beta$-unsaturated ketone to be separated, if desired, by distillation from the reaction mixture. However, in the production of the propargyl alcohol of this invention, it is generally not necessary to separate the two ketones (IV and V) from each other.

The production of a substituted propargyl alcohol of formula (III) from the $\alpha,\beta$-unsaturated ketone is accompanied by the isomerization of said ketone to the $\beta,\gamma$-unsaturated ketone of formula (IV). This isomerization can be performed in an independent reaction system, prior to the ethynylation reaction by heating the ketone in the presence of an acid catalyst. The isomerization may be applied to the $\alpha,\beta$-unsaturated ketone per se or to a mixture of the ketones containing $\alpha,\beta$-unsaturated ketone in an amount in excess of the amount at thermal equilibrium with $\beta,\gamma$-unsaturated ketone. Alternatively, since the $\beta,\gamma$-unsaturated ketone is lower-boiling as compared with the $\alpha,\beta$-unsaturated ketone, a mixture of the two ketones can be distilled under the conditions suited for the isomerization of $\alpha,\beta$-unsaturated ketone, whereby the $\beta,\gamma$-unsaturated ketone alone can be continuously obtained as the distillate. In the separation and recovery of the $\beta,\gamma$-unsaturated ketone by distillation after or during the isomerization stage, the acid isomerization catalyst is preferably an acid having a higher boiling point than the $\beta,\gamma$-unsaturated ketone. Examples of such acid are aliphatic or aromatic sulfonic acids such as benzenesulfonic acid, p-toluenesulfonic acid, laurylsulfonic acid, etc.; monocyclic, aromatic or alicyclic mono-, di- or polycarboxylic acids which may contain a hetero-atom such as p-toluic acid, 4-nitro-m-toluic acid, 4-hydroxybenzoic acid, vanillic acid, 4-nitroisophthalic acid, cyclohexanecarboxylic acid, etc.; saturated or unsaturated aliphatic or heteroaliphatic mono-, di- or polycarboxylic acids which may have a hydroxyl group or a phenyl substituent such as adipic acid, 1,2-hydroxystearic acid, benzylic acid, p-nitrocinnamic acid, diglycolic acid, etc.; aliphatic or aromatic amino acids such as indolebutyric acid, 1,2-diaminocyclohexanetetra acetic acid, etc.; and inorganic acids such as metaphosphoric acid, phenylphosphinic acid and the like. The amount of said acid catalyst depends upon the type of catalyst. For example, sulfonic acids can be used in the range of 0.01 to 0.1 mole percent with respect to the $\alpha,\beta$-unsaturated ketone. Generally the other acids may be in the range of 0.1 to 20 mole percent and, preferably, in the range of 4 to 8 mole percent based on the $\alpha,\beta$-unsaturated ketone.

Another method for isomerization of the $\alpha,\beta$-unsaturated ketone involves contacting the ketone with a base in a separate system prior to the ethynylation reaction. The $\alpha,\beta$-unsaturated ketone can be used alone or in admixture with the $\beta,\gamma$-unsaturated ketone. The aforementioned base is exemplified by alkalies such as alkali metal hydroxides, e.g. sodium hydroxide, lithium hydroxide, potassium hydroxide, cesium hydroxide, alkaline earth metal hydroxides, e.g., calcium hydroxide and barium hydroxide, weak acid salts of alkali metals, e.g., sodium carbonate, potassium carbonate, sodium acetate and potassium acetate, weak acid salts of alkaline earth metals, e.g., calcium carbonate and magnesium carbonate, alkali metal amides, e.g., lithium amide, sodium amide and potassium amide, alkali metal alcoholates, e.g., sodium methoxide, sodium ethyoxide, sodium tert.-butoxide and potassium tert.-butoxide, and organic nitrogen-containing bases including tertiary amines, secondary amines and cyclic imines, e.g., triethylamine, monoethanolamine, diethanolamine, triethanolamine, 1,5-diazabicyclo-[3.4.0]nonene-5, 1,5-diazabicyclo-[5.4.0]-undecene-5 (abbreviated as DBU), 2-dimethylamino-1-pyrroline, 1,4-diazabicyclo-[2.2.2]octane (abbreviated as DABCO), 5-methyl-1-azabicyclo-[3.3.0]octane and hexamethylenetetramine. The solid bases are preferably dissolved in a suitable solvent such as liquid ammonia, N-methylpyrrolidone, dimethylformamide, dimethylsulfoxide, methanol or ethanol. If water-soluble, such bases may also be used as aqueous solutions. Alkali metal hydroxides are particularly desirable among alkali- and alkaline earth metal-containing bases in terms of the rate of isomerization reaction, when used as a 20 to 60 weight percent solution in water and in combination with a quaternary ammonium salt or phosphonium salt, i.e., the catalyst previously mentioned in connection with the reaction of an organic halide R-halo. with mesityl oxide and/or isomesityl oxide. The catalyst can be employed in the range of 0.001 to 10 mole percent based on the alkali metal hydroxide employed, although the range of 0.1 to 3 mole percent is particularly preferred. The proportion of the base can be optionally selected, on a weight basis, from the range of 1 to 400 weight percent based on the weight of $\alpha,\beta$-unsaturated ketone, with other parameters such as reaction velocity, reaction temperatures and economics also being considered. The preferred reaction temperature is somewhere between 50° and 200° C. for organic nitrogen-containing bases, and between $-10°$ and $+100°$ C. for other bases. The bases which are most preferably employed in the practice of this invention are organic nitrogen-containing strong bases such as DBU and DABCO and aqueous solutions of sodium hydroxide or potassium hydroxide. After the isomerization reaction, the $\alpha,\gamma$-unsaturated ketone may be separated from the reaction mixture by distillation. Alternatively, the distillation of the mixture of the ketones under the conditions of isomerization reaction may be employed with the use of such a base (e.g., DBU) that has a higher boiling point than $\alpha,\beta$- and $\beta,\gamma$-unsaturated ketones and that enables a high rate of isomerization, whereby $\beta,\gamma$-unsaturated ketone can be obtained continuously.

2. Production of the substituted propargyl alcohol

It is known that compounds having the propargyl alcohol structure may be produced by the ethynylation of ketones. In this connection, reference is made to U.S. Pat. Nos. 3,082,260, 3,496,240 and U.S. Published Patent application No. B 460,846, and "Acetylenic Compounds, Preparation and Substitution Reactions" by Thomas F. Rutledge (Reinhold Book Corp., 1968).

In the production of a substituted propargyl alcohol of formula (III) of this invention, the ethynylation of $\beta,\gamma$-unsaturated ketone of formula (IV) or a mixture of said ketone (IV) and $\alpha,\beta$-unsaturated ketone of formula (V) may be performed by a known procedure. As preferred examples of such ethynylation procedures the following are representative:

a. The reaction of the ketones with acetylene in contact with a catalytic amount of a strongly basic compound of alkali metal and in an organic polar solvent which is not involved in the reaction such as N,N-dimethylformamide, dimethylsulfoxide, N-methylpyrrolidone, tetrahydrofuran, dimethyl ether, diethyl ether, methyl ethyl ether, anisole or dioxane.

b. The reaction of the ketones with acetylene in the same manner as (a) above except that liquid ammonia is employed as the solvent in lieu of an organic polar solvent.

c. The reaction of the ketones with acetylene in the same manner as (a) above except that a mixture of liquid ammonia and an organic polar solvent is employed as the solvent.

The aforementioned ethynylation processes are more advantageous than ethynylation processes which involve the use of a Grignard reagent such as an ethynylmagnesium halide or an acetylide of alkali metal or alkaline earth metal in that the production of propargyl alcohol is economical and requires only a simple separation technique. In terms of solvent recovery and product separation, the above process (b) is particularly desirable. The strongly basic compounds of alkali metals, suitable for use as catalyst, are sodium and potassium hydroxides; sodium and potassium alkoxides containing 1 to 5 carbon atoms such as sodium methoxide, sodium ethoxide, sodium butoxide, potassium ethoxide, potassium butoxide, etc.; and sodium and potassium amides, and they may be employed alone or as mixtures. Particularly preferred are the potassium compounds. It is possible to add precursors capable of forming the aforementioned basic compounds in situ in the reaction system. These basic compounds may be dissolved in water, alcohol or other solvents before being added to the reaction system. While there is no particular limitation on the amount of such compound, it is preferable, for the purpose of commercial production, that the compound be used in the range of 0.1 to 30 mole percent and, for still better results, 1 to 10 mole percent based on the unsaturated ketone. Generally, the reaction is conducted by contacting acetylene with a solution of the unsaturated ketone in a solvent in the presence of said alkali metal compound. The reaction solvent is preferably employed in a volume at least equal to that of the unsaturated ketone, the range of 2 to 20 times the volume of the unsaturated ketone being particularly desirable.

Reference to the prior art, for example, U.S. Published Pat. application No. B 460,846, might suggest that the ethynylation of $\alpha,\beta$-unsaturated ketone in the present invention would give a substituted propargyl alcohol of said formula (III'). However, when said ethynylation reaction is conducted by the process (a), (b) or (c) mentioned above, the isomerization of $\alpha,\beta$-unsaturated ketone of formula (V) to $\beta,\gamma$-unsaturated ketone may take place advantageously in the ethynylation reaction system. Further studies have indicated that this phenomenon is specific to the $\alpha,\beta$-unsaturated ketone having a hydrocarbon substituent such as the group R hereinbefore mentioned in the position alpha to the carbonyl group. The amount of acetylene may be at least about 0.5 mole, preferably from 1 to 20 moles per mole of the total of $\alpha,\beta$- and $\beta,\gamma$-unsaturated ketones. Therefore, where the ethynylation reaction is carried out by the above processes (a) to (c), the unsaturated ketone to be thus reacted may not only be the $\beta,\gamma$-unsaturated ketone or a mixture of $\beta,\gamma$-unsaturated ketone and $\alpha,\beta$-unsaturated ketone but also be the $\alpha,\beta$-unsaturated ketone alone. This means that it is not necessary to separate and remove the $\alpha,\beta$-unsaturated ketone from the mixture of $\alpha,\beta$-unsaturated ketone and $\beta,\gamma$-unsaturated ketone obtained by the reaction of an organic halide R-halo. with mesityl oxide and/or isomesityl oxide. Nor is it necessary to subject the ketone to a separate isomerization reaction. The reaction temperature may range from $-33°$ C. to $+30°$ C. and, preferably, from −15° C. to +15° C. The increase in the amount of acetylene used in the reaction aids in promoting the conversion of β,γ-unsaturated ketone (IV) to propargyl alcohol (III), and suppressing the diethynylation reaction of the formed propargyl alcohol to β,γ-unsaturated ketone of formula (IV). In this case, the production of a propargyl alcohol of formula (III') structurally corresponding to the α,β-unsaturated ketone is minimized.

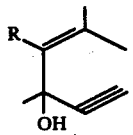

(III')

wherein R is as defined hereinbefore.

The propargyl alcohols, allylic alcohols and δ,ε-unsaturated ketones according to this invention not only have the perfume utility inherent in themselves but are important precursors as closely associated intermediates in the production of terpenoid compounds.

After the ethynylation reaction, the unreacted β,γ-unsaturated ketone (IV) and/or α,β-unsaturated ketone (V) and/or such ketones that might be contained in the reaction mixture as originating from the isomerization reaction may be recovered by distillation and subjected to the isomerization reaction and/or ethynylation reaction to obtain an additional amount of the propargyl alcohol.

Preferred examples of the propargyl alcohols of formula (III) which can thus be obtained by said ethynylation reaction are those which contain the preferred groups R mentioned hereinbefore. Representative of the alcohols having formula (III) are as follows:
4-Isopropenyl-3-methyl-1-octyn-3-ol,
4-Isopropenyl-3,7-dimethyl-1-octyn-3-ol,
4-Isopropenyl-3,7-dimethyl-1-octyn-6-en-3-ol,
4-Isopropenyl-3,7-dimethyl-1-octyn-7-en-3-ol,
4-Isopropenyl-3,7-dimethyl-1-nonyn-6-en-3-ol,
4-Isopropenyl-3,7,11-trimethyldodeca-1-yn-3-ol,
4-Isopropenyl-3,7,11-trimethyldodeca-1-yn-6,10-dien-3-ol,
4-Isopropenyl-3,7,11-trimethyldodeca-1-yn-10-en-3-ol,
4-Isopropenyl-3,7,11-trimethyldodeca-1-yn-6-en-3-ol,
4-Isopropenyl-3,11-dimethyl-7-ethyltrideca-1-yn-6,10-dien-3-ol,
4-Isopropenyl-3,7,11-trimethyldodeca-1-yn-3,11-diol,
4-Isopropenyl-3,7,11-trimethyl-11-methoxydodeca-1-yn-3-ol,
4-Isopropenyl-3,6,7-trimethyl-1-octyn-3,7-diol,
4-Isopropenyl-3,6,7-trimethyl-7-methoxy-1-octyn-3-ol,
4-Isopropenyl-3,6,7-trimethyl-1-octyn-6-en-3-ol,
4-Isopropenyl-3,6,7-trimethyl-1-octyn-7-en-3-ol,
4-Isopropenyl-3,6,7-trimethyl-1-nonyn-6-en-3-ol, and
4-Isopropenyl-6-ethyl-3,7-dimethyl-1-octyn-3-ol B. Allylic Alcohols and Methods For The Production of Same The allylic alcohols of this invention which are represented by the general formula (II):

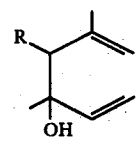

(II)

wherein R is as defined hereinbefore, is produced by partial hydrogenation of the propargyl alcohol of formula (III). It is well known that the carbon-to-carbon triple bond is preferentially hydrogenated to the carbon-to-carbon double bond and, in accordance with this invention, use is made of conventional hydrogenation processes used for this purpose.

1. Partial hydrogenation

One known hydrogenation process comprises a partial hydrogenation of the propargyl alcohol with a hydrogenating agent such as lithium aluminum hydride. In another known process, the propargyl alcohol is catalytically reduced by $H_2$ in the presence of a suitable hydrogenation catalyst in the presence or absence of a solvent such as a saturated aliphatic hydrocarbon, an aromatic hydrocarbon and an alcohol. Suitable solvents include n-hexane, n-heptane, octane, benzene, toluene, xylene, methanol, ethanol, propanol or the like. The latter process is commercially preferred and generally the substituted propargyl alcohol is partially hydrogenated under mild conditions, for example, at a temperature of 0° to 130° C. and at pressures ranging from atmospheric to 50 kg/cm² gauge. The preferred hydrogenation catalyst is exemplified by nickel, cobalt, palladium, platinum, rhodium or iridium, compounds of these metals, or such metal or compound supported on a carrier, for example, active carbon, barium sulfate or calcium carbonate, and the like. Particularly desirable is the Lindlar catalyst consisting of palladium metal supported on calcium carbonate. The selectivity of the partial hydrogenation reaction may be enhanced by adding a small amount of an organic nitrogen-containing compound, e.g., quinoline or triethylamine, to the reaction system.

2. Grignard reagent

The allylic alcohol of this invention may also be produced by reacting a β,γ-unsaturated ketone of formula (IV) with a vinyl-Grignard reagent such as a vinylmagnesium halide by a known method. This method is most preferred if high purity of the allylic alcohol is desired.

In either of the above methods for the production of the allylic alcohol, the β,γ-unsaturated ketone of formula (IV) and/or the α,β-unsaturated ketone of formula (V) which may remain unreacted, may be separated from the reaction mixture by distillation and recycled for use in the production of the propargyl alcohol.

Preferred examples of the substituted allylic alcohol of formula (II) have preferred groups as previously defined in R. Typical of the preferred allylic alcohols are:
4-Isopropenyl-3-methyl-1-octen-3-ol,
4-Isopropenyl-3,7-dimethyl-1-octen-3-ol,
4-Isopropenyl-3,7-dimethyl-1,6-octadien-3-ol,
4-Isopropenyl-3,7-dimethyl-1,7-octadien-3-ol,
4-Isopropenyl-3,7-dimethyl-1,6-nonadien-3-ol,
4-Isopropenyl-3,7,11-trimethyldodeca-1-en-3-ol,
4-Isopropenyl-3,7,11-trimethyldodeca-1,6,10-trien-3-ol,
4-Isopropenyl-3,7,11-trimethyldodeca-1,10-dien-3-ol, 4-Isopropenyl-3,7,11-trimethyldodeca-1,6-dien-3-ol,
4-Isopropenyl-3,11-dimethyl-7-ethyltrideca-1,6,10-trien-3-ol,
4-Isopropenyl-3,7,11-trimethyldodeca-1-en-3,11-diol, and
4-Isopropenyl-3,7,11-trimethyl-11-methoxydodeca-1-en-3-ol.

C. δ,ε-Unsaturated Ketones and Method For The Production of Same

In accordance with this invention, the δ,ε-unsaturated ketone of formula (I):

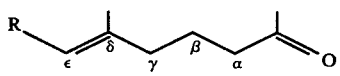
(I)

wherein R is as defined hereinbefore, which may be produced by a rearrangement reaction which comprises heating an allylic alcohol of formula (II). This rearrangement reaction may be conducted in a liquid phase or a gaseous phase. The reaction temperature may range from 100° to 400° C., the preferred temperature range is from 130° to 230° C. for the liquid-phase reactions. In gaseous phase, the reactions preferred range from 250° to 400° C., although the optimum temperature depends upon the residence time. The reaction can be conducted in the atmosphere, i.e., an atmosphere containing molecular oxygen. However, it is generally preferable to conduct the reaction in an inert gaseous atmosphere such as nitrogen or helium. There is no particular limitation on the reaction pressure, the reaction proceeds satisfactorily at atmospheric pressure. However if the reaction is carried out in gaseous phase and where, in the liquid-phase reaction, the boiling point of the allylic alcohol of formula (II) or the reaction solvent is lower than the reaction temperature, it is preferable that the reaction be conducted at reduced or elevated pressures appropriate to the other reaction parameters.

Although the use of a solvent is not critical in the liquid-phase reaction, a solvent which is stable under the conditions of rearrangement reaction, and which is inert to the reaction or which increases the selectivity of the rearrangement, can be used. In this connection, it has been found that the certain organic nitrogen-containing solvents improve the selectivity to the rearrangement reaction and renders the reaction more efficient. The organic nitrogen-containing solvent is defined as a solvent in terms of nuclear magnetic resonance spectrometry, wherein 10 mg of the solvent is added to 0.5 ml of a solution (10% by volume) of the allylic alcohol of formula (II) in deuteriodimethylsulfoxide having a purity of more than 99.5 weight percent and containing water as a contaminant, the proton exchange time, i.e., the time of proton exchange between the hydroxyl proton of the allylic alcohol and the proton of the solvent or between the protons of water occurring in a minor amount in said deuteriodimethylsulfoxide and the hydroxyl proton of said allylic alcohol will not be less than $5 \times 10^{-2}$ seconds at a temperature of 30° C. and not less than $10^{-2}$ seconds at 100° C. In this regard, the shape [g(ν)] of the NMR spectrum, with chemical shifts being taken into account, is theoretically a function of $\zeta A$, $\zeta B$, $\nu A$ and $\nu B$, where A is the exchange site (i.e., hydroxyl proton) on the allylic alcohol; B is the exchange site on the water or solvent; $\zeta A$ and $\zeta B$ are the times during which the protons are detained at the sites A and B, respectively; and $\nu A$ and $\nu B$ are the chemical shifts of A and B, respectively. Assuming, further, that $\zeta A = \zeta B = 2\zeta$ and that the line width has no dimension throughout the process except for the exchange, the following equation holds.

$$g(\nu) = K \frac{\zeta(\nu A - \nu B)^2}{[\frac{1}{2}(\nu A - \nu B) - \nu]^2 + 4\pi^2 \zeta^2 (\nu A - \nu)^2 (\nu B - \nu)^2}$$

$$K = \int_{-\infty}^{\infty} g(\nu) d\nu$$

The proton exchange time (referred to as ζo) can be arrived at by comparing the values obtained by calculating the line shape with νA−νB=90 Hz and on variation in the value of 2 πζ(νA−νB) from 100 to 0.1 with the measured value of the line shape. It is to be noted that since ζo varies slightly with the conditions of NMR determination, the purity of deuteriodimethylsulfoxide, etc., the accuracy of the value is about 80 percent.

The organic nitrogen-containing solvents satisfying the above conditions are typically the compounds containing

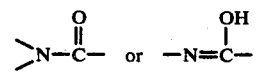

groups such as N,N-dimethylformamide, N,N-dimethylacetamide, 2-pyrrolidone, N-methyl-2-pyrrolidone, N-ethyl-2-pyrrolidone, 3,3,5-trimethyl-2-pyrrolidone, ε-caprolactam, N-alkylcaprolactams (e.g., N-methyl-ε-caprolactam, N-ethyl-ε-caprolactam), N-acetylanilide, N-acetyl-O-aminoanisole and oxyindole, etc.; the compounds containing

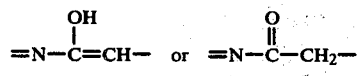

groups or analogues thereof such as 2-hydroxypyridine, 2-methoxypyridine, pyridine-2-thiol, 2-methylmercaptopyridine, etc.; compounds containing

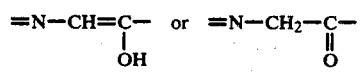

groups or analogues thereof such as 3-hydroxypyridine, pyridine-3-thiol, 3-pyrrolidone, indoxyl, etc.; compounds containing —N=CH—NH— group such as benzimidazoles, etc.; compounds containing

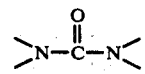

group such as diphenylurea, ethyleneurea, ethylenethiourea, etc.; and tertiary aromatic amines such as triphenylamine, dimethylaniline and diethylaniline.

Generally, the rearrangement of the allylic alcohols of formula (II) is preferably conducted with a weight ratio of said solvent to said alcohol within the range of 0.1 to 10 and, preferably in the range of 0.5 to 3, in an inert gaseous atmosphere and by heating at a temperature in the range of 130° to 230° C. and, preferably in the range of 150° to 210° C.

The rearrangement of an allylic alcohol to the corresponding unsaturated ketone by heating is known as Oxy-Cope Rearrangement. However, the particular allylic alcohols according to this invention have not been subjected to the Oxy-Cope rearrangement reaction prior to the present invention, nor is it known that the corresponding ketones were produced in this manner. The prior art pertinent to Oxy-Cope Rearrangement reaction will be briefly reviewed. The Oxy-Cope Rearrangement was studied with cyclic compounds [J. A. Berson et al, J. Am. Chem. Soc. 86, 5017 and 5019 (1964)] and gas-phase reactions of acyclic compounds [A. Viola et al, J. Am. Chem. Soc. 87, 1150 (1965)]. The report of A. Viola et al in J. Am. Chem. Soc. 89, 3462 (1967) is most pertinent in the explaining of the effect of the position of the substituent in the Oxy-Cope Rearrangement. According to this literature reference, a compound corresponding to general formula (II) where R is a hydrogen atom, is subjected to an Oxy-Cope Rearrangement reaction at a temperature of from 370° to 380° C. and a corresponding δ,ε-unsaturated ketone in a yield of 42% was obtained. Other work relative to the Oxy-Cope Rearrangement included an attempt to protect the hydroxyl group with an alkyl radical [J. Am. Chem. Soc. 90, 4729 (1968)] and with a triemthylsilyl radical [J. Chem. Soc., Chem. Commun., 237 (1971)] to control the decomposition reaction. It has recently been reported that Oxy-Cope Rearrangment yields high selectivity at low temperature and in reduced reaction time if the hydroxyl group is protected with a metal and crown ether is used as a catalyst [D. A. Evans et al, J. Am. Chem. Soc. 97, 4765 (1975)]. Generally, the Oxy-Cope Rearrangement reaction has several disadvantages; it involves decomposition and other side reactions which diminish the yield of desired δ,ε-unsaturated ketone. However, these attempts to inhibit the decomposition reaction by protecting the hydroxyl group has been time-consuming and expensive. It is for these reasons that no commercial application of the Oxy-Cope Rearrangement reaction has materialized.

The rearrangement reaction of the allylic alcohols of formula (II) may be schematically illustrated below:

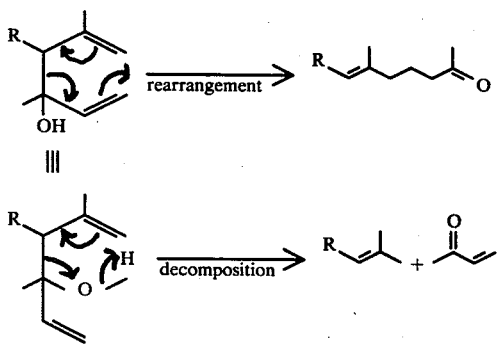

As shown above, the rearrangement reaction takes place as the electron shift occurs between the double bonds, whereas the decomposition reaction proceeds as the electron shift occurs between the double bond and the hydroxyl group. And in both the gaseous-phase and liquid-phase reactions, the ratio of the rearrangement product to the decomposition product is normally about 60-70:40-30. The rearrangement product is the δ,ε-unsaturated ketone which is a structural isomer of the starting allylic alcohol. It should be pointed out that in the method of this invention, any double bond in group R is not involved in the rearrangement and that the [1,3]-sigmatropic reaction and the other undesired side reactions which are normally associated with the Oxy-Cope Rearrangement are avoided.

The following are some preferred examples of the δ,ε-unsaturated ketones which can be produced according to this invention:
6,10-Dimethyl-6,9-undecadien-2-one,
6,10-Dimethyl-6-undecene-2-one,
6,10-Dimethyl-6,10-undecadien-2-one,
6,10,14-Trimethyl-6,9,13-pentadecatrien-2-one,
6,10,14-Trimethyl-6,9-pentadecadien-2-one,
6,10,14-Trimethyl-6,9,14-pentadecatrien-2-one, and
6,10,14-Trimethyl-6,9-pentadecadien-14-ol-2-one.

The group R designated by the following formula is most preferably employed in the application of this invention and will be described hereinbelow.

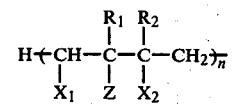

In one form of this structure, either $X_1$ or $X_2$ is a hydrogen atom, the other jointly with Z represents a bond; Z jointly with $X_1$ or $X_2$ represents a bond; $R_1$ is methyl; $R_2$ is hydrogen; and n is a whole number of 1. This form may be designated by the following general formula (A):

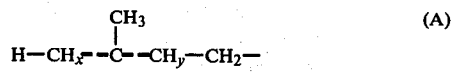

In the above formula (A), the dotted line means that, at the position indicated, the bond is either a single or a double bond, one double bond being present, and each of x and y is 1 or 2, the value of x and of y being dictated by the position of the double bond. In another form, either $X_1$ or $X_2$ in group R is a hydrogen atom, the other jointly with Z represents a bond; Z jointly with $X_1$ or $X_2$ represents a bond; $R_1$ is methyl; $R_2$ is hydrogen; n is 2; and $X_1$ and $X_2$ may be the same or different. This form may be represented by the following general formula (B):

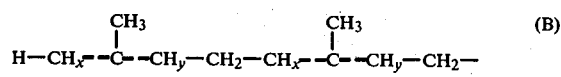

Referring to the above formula (B), except that the first occurring x and y may be the same as or different from the second occurring x and y, respectively, the dotted line, x, and y are as defined for the formula (A). The δ,ε-unsaturated ketones of the formula:

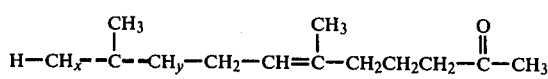

which are obtainable via the substituted propargyl alcohol and allylic alcohol having a group of the above formula (A) as intermediates may for example be reacted with diacetylene and the reaction product may then be subjected to hydrogenolysis, whereby squalane which is of use as a cosmetic basis may be easily obtained (see U.S. Pat. No. 3,923,918).

The δ,ε-unsaturated ketones of the formula:

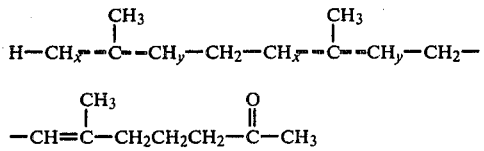

which are obtainable via the substituted propargyl alcohol having a group of the above formula (B) may be converted to isophytol which is a starting material for vitamine E, for example, by hydrogenation, ethynylation of the hydrogenated intermediates and partial hydrogenation of the ethynylated precursor.

The invention will now be described in connection with the following examples in which parts and percentages are by weight unless otherwise indicated. In the examples, "Released system" means the ethynylation reaction under atmosphere pressure while bubbling acetylene through the reaction system.

EXAMPLE 1

1. Production of the α,β- and β,γ-unsaturated ketones

To a solution of 600 g of sodium hydroxide in 490 g of water were added 980 g of mesityl oxide, 520 g of prenyl chloride and 25 g of trimethylstearylammonium chloride. The resulting mixture was reacted with stirring for 2 hours in a water bath. The reaction temperature was maintained at 70° C. Upon completion of this reaction, the reaction mixture was poured into a container of water and the resulting aqueous solution was extracted with ethyl ether. The ethereal solution was first washed with water and then dried over anhydrous sodium sulfate. The ether was distilled off under reduced pressure and the residue (1250 g) was further distilled to recover the unreacted mesityl oxide. The distilland contained 560 g of a mixture of 3-isopropenyl-6-methyl-5-hepten-2-one and 3-isopropylidene-6-methyl-5-hepten-2-one (purity 96.4%) in a ratio of 2.5 to 1. Based on the purity of 83.71% for the prenyl chloride used, the yield of 3-isopropenyl-6-methyl-5-hepten-2-one was 59% (410 g) and that of 3-isopropylidene-6-methyl-5-hepten-2-one was 19% (130 g).

The above mixture of unsaturated ketones was distilled in a rectifying column with 30 theoretical plates, and 3-isopropenyl-6-methyl-5-hepten-2-one was obtained from a forerunning distillate at bp. 32°–34° C./0.2 mmHg, with 3-isopropylidene-6-methyl-5-hepten-2-one being obtained from the after-running distillate at bp. 35°–38° C./0.2 mmHg. The major component of the mixture 3-isopropenyl-6-methyl-5-hepten-2-one has the structural formula:

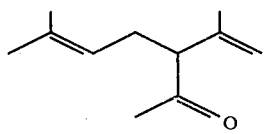

The structural identification of these ketones was performed by the following methods:
Infrared absorption spectrum:

(cm$^{-1}$) 1714 (>C=O), 1642 (>C=C<), 1445, 1378, 1353, 1153, 900

Nuclear magnetic resonance spectrum (δinCCl$_4$ppm):

| 1.57, 1.58 | (each s | 9H, CH$_3$—) |
| 1.99 | (s | 3H, CH$_3$C—<br>∥<br>O) |
| 2.03–2.40 | (m | 2H, —CH$_2$—) |
| 3.07 | (t | 1H, —C—CH—<br>∥<br>O) |
| 4.85, 4.89 | (each s | 2H, =CH$_2$) |
| 4.95 | (t | 1H, =CH—) |

Isopropylidine-6-methyl-5-hepten-2-one has the structural formula:

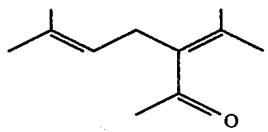

Infrared absorption spectrum (cm$^{-1}$):
1688 (>C=O), 1615 (>C=C<), 1440, 1375, 1350, 1278, 1202, 1170, 975, 935, 850

Nuclear magnetic resonance spectrum (δinCCl$_4$ppm):

| 1.62, 1.70, 1.75 | (each s, | 12H, CH$_3$—) |
| 2.05 | (s, | 3H, CH$_3$C—<br>∥<br>O) |
| 2.88 | (d, | 2H, —CH$_2$—) |
| 4.97 | (t, | 1H, —CH=C<) |

2. Isomerization of the α,β-unsaturated ketone

The above produced 3-isopropylidene-6-methyl-5-hepten-2-one (130 g) together with 7 g of trans-1,2-cyclohexanedicarboxylic acid was fed into the bottom of a rectifying column with 50 theoretical plates and distilled at a reduced pressure of 30 mm Hg with a reflux ratio of 30:1, yielding 107 g of distillate. Gas chromatographic analysis of this distillate confirmed a mixture of 3-isopropenyl-6-methyl-5-hepten-2-one (94%) and 3-isopropylidene-6-methyl-5-hepten-2-one (6%). This reaction product was combined with 410 g of 3-isopropenyl-6-methyl-5-hepten-2-one previously obtained and was ethynylated as described below in 3.

3. Production of substituted propargyl alcohol

Into a three-necked flask of 5-liter capacity, 70 g of sodium metal was added to 3 liters of liquid ammonia. Acetylene gas was then bubbled through this mixture. When the reaction mixture turned a grey color, the introduction of acetylene gas was suspended and 517 g of the 3-isopropenyl-6-methyl-5-hepten-2-one (containing a small amount of 3-isopropylidene-6-methyl-5-hepten-2-one) was added. Then, bubbling acetylene gas through the reaction system maintained at −33° C., the reaction was continued for 3 hours. Following removal of the ammonia, the reaction mixture was neutralized with ammonium chloride, water was added and then the resulting mixture was extracted with ether. The ethereal solution was dried over sodium sulfate and the solvent was distilled off under reduced pressure. The residue weighing 524 g was distilled under reduced pressure to recover 519 g of a distillate at bp. 59°–61° C./0.5 mm Hg. This distillate was a mixture of 3-isopropenyl-6-methyl-5-hepten-2-one (2 weight percent), 3-isopropylidene-6-methyl-5-hepten-2-one (8 weight percent) and chiefly 4-isopropenyl-3,7-dimethyl-6-octen-1-yn-3-ol (90 weight percent) having the structural formula:

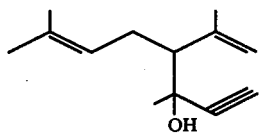

The structural identification of the main product was carried out by the following methods:
Infrared absorption spectrum (cm$^{-1}$):
3440 (—OH), 3300, 2120, 1640, 1450, 1378, 1128, 1030, 900
Nuclear magnetic resonance spectrum (δinCCl$_4$ppm):

| 1.40 | (s, 3H, CH$_3$—C—)<br>\|<br>O— |
| --- | --- |
| 1.60 | (s, 6H, CH$_3$—) |
| 1.72, 1.73 | (each s, 3H, CH$_3$—) |
| 2.00–2.47 | (m, 3H, —CH$_2$—CH—) |
| 2.30 | (s, 1H, —C≡CH) |
| ca, 4.83–5.00 | (m, 3H, =CH—, =CH$_2$) |

4. Production of the allylic alcohol

A solution of 500 g of 4-isopropenyl-3,7-dimethyl-6-octen-1-yn-3-ol in 1.5 liters of n-hexane was hydrogenated at ambient temperature and atmospheric pressure using 25 g of 0.25% Lindlar catalyst. The reaction was sequentially monitored by gas chromatography (PEG20M, 150° C.) and the reaction was terminated when no starting material remained. The catalyst was filtered off and the solvent was removed from the filtrate by distillation under reduced pressure. The residue was distilled in vacuo to obtain 482 g of 4-isopropenyl-3,7-dimethyl-1,6-octadien-3-ol as a fore-running distillate at bp. 55°–59° C./0.4 mm Hg.

The allylic alcohol has the formula:

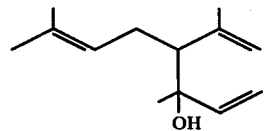

The residual fraction was further distilled under high vacuum to obtain 12 g of a distillate boiling at 77°–82° C./0.15 mm Hg. The following analysis showed that this distillate consisted of 6,10-dimethyl-6,9-undecadien-2-one, having the formula:

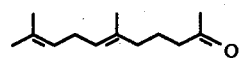

Infrared absorption spectrum (cm$^{-1}$):
3480 (—OH), 1638 (>C=C<), 1450, 1376, 998, 922, 895
Nuclear magnetic resonance spectrum (δinCCl$_4$ppm):

| 1.13 | (s, 3H, CH$_3$—) |
| --- | --- |
| 1.53, 1.62, 1.66 | (broad s, 9H, CH$_3$—) |
| ca 1.90–2.20 | (m, 3H, —CH$_2$—CH—) |
| ca 4.60–5.02 | (m, 4H, =CH$_2$, =CH—, H H / H*) |
| 5.12 | (dd, 1H, H* / H) |
| 5.85 | (dd, 1H, H / H*) |

Infrared absorption spectrum (cm$^{-1}$):
1715 (>C=O), 1675 (>C=C<), 1445, 1360, 1158, 1107, 985, 935, 827
Nuclear magnetic resonance spectrum (δinCCl$_4$ppm):

| 1.55, 1.60 | (each s, 9H, CH$_3$—) |
| --- | --- |
| ca 1.68–2.40 | (m, 6H, —CH$_2$CH$_2$CH$_2$—) |
| 1.96 | (s, 3H, CH$_3$C—)<br>\|\|<br>O |
| 2.59 | (t, 2H, =C—CH$_2$—C=) |
| 5.05 | (t, 2H, =CH—) |

5. Production of the δ,ε-unsaturated ketone

Into a three-necked flask of 1 liter capacity, 482 g of 4-isopropenyl-3,7-dimethyl-1,6-octadien-3-ol, obtained as described in (4) above as the fore-running distillate, was introduced and heated in a nitrogen atmosphere. The rearrangement reaction was maintained at temperatures of 170°–180° C. for 4 hours. The reaction mixture was distilled in vacuo to remove 140 g of a mixture of 2,6-dimethylhepta-2,5-diene, which is a decomposition product, and 3-isopropenyl-6-methyl-5-hepten-2-one and 3-isopropylidene-6-methyl-5-hepten-2-one, which are impurities in the starting material, as the low-boiling fraction. As a higher-boiling product (bp. 75°–77° C./0.5 mm Hg) 331 g of crude, 6,10-dimethyl-6,9-undecadien-2-one was obtained. This unsaturated ketone was structurally identified by:

a. the fact that the product of hydrogenation with 5% palladium-on-carbon agreed with an authentic sample of 6,10-dimethylundeca-2-one in gas chromatographic retention time and nuclear magnetic resonance spectrum; and b. the fact that the main products of ozonolysis were 4-methyl-3-penten-1-al [mass spectrum: 98, 69, 41]

and heptane-2,6-dione [mass spectrum: 128, 110, 95, 85, 71, 58, 43].

EXAMPLE 2

The reaction procedure described in Example 1, Section 1, under the title of "Production of the α,β-and β,γ-unsaturated ketones" was repeated except that 980 g of a 85:15 mixture of isomesityl oxide and mesityl oxide was employed in lieu of 980 g of mesityl oxide. The reaction mixture was poured into a container of water and the resulting aqueous solution extracted with ether. The solvent was removed from the ethereal layer and the residue (1250 g) was distilled to recover the unreacted isomesityl oxide and mesityl oxide (ratio 6:94). As a higher-boiling product was obtained 560 g of a mixture of 3-isopropenyl-6-methyl-5-hepten-2-one and 3-isopropylidene-6-methyl-5-hepten-2-one in a 2.5 to 1 ratio.

The above mixture was distilled in the same manner as in Example 1 to obtain 130 g of 3-isopropylidene-6-methyl-5-hepten-2-one as an after-running distillate. This distillate was then transferred to an autoclave and to 130 g of this distillate 1500 ml of liquid ammonia was introduced and a solution of 2.2 g of potassium hydroxide in 8 ml of a water as a catalyst was added. Acetylene gas was bubbled into the system to give a total pressure at 0° C. of 11 kg/cm², the ethynylation reaction was continued at 0° C. for 1 hour. Upon completion of the reaction, the reaction mixture was neutralized with ammonium chloride and the ammonia was removed. The residue was poured into a container of water and the resulting aqueous solution was extracted with ether. The ethereal extract was dried over sodium sulfate and the ether was then removed. The residue was distilled under reduced pressure to obtain 130.7 g of distillate. Gas chromatographic analysis of this distillate showed that it was a mixture of 3-isopropenyl-6-methyl-5-hepten-2-one (8.4 weight percent), 3-isopropylidene-6-methyl-5-hepten-2-one (26.4 weight percent), 4-isopropenyl-3,7-dimethyl-6-octen-1-yn-3-ol (64.6 weight percent) and misc., (0.6 weight percent).

EXAMPLES 3-7

Mixtures containing different proportions of the 3-isopropenyl-6-methyl-5-hepten-2-one and 3-isopropylidene-6-methyl-5-hepten-2-one compounds prepared in Example 1, were ethynylated under varying conditions to synthesize samples of 4-isopropenyl-3,7-dimethyl-6-octen-1-yn-3-ol. The proportions, conditions and results are summarized in Table I.

All the reactions involved the use of 12.45 g of a mixture of 3-isopropenyl-6-methyl-5-hepten-2-one and 3-isopropylidene-6-methyl-5-hepten-2-one and, as the solvent, 150 ml of liquid ammonia in an autoclave.

TABLE I

| EXAMPLE | Composition of starting ketone (V)/(IV) | Catalyst solution | CH≡CH pressure (Total pressure) | Conditions of reaction | Composition of reaction mixtures | | | |
|---|---|---|---|---|---|---|---|---|
| | | | | | (V) % | (IV) % | (III) % | Misc. |
| 3 | 35.5/64.5 | KOH 0.21 g CH₃OH 10 ml | 7.3 kg/cm² (at 6° C.) | 6° C., 6 hr. | 20.6 | 7.0 | 71.6 | 0.8 |
| 4 | 82.4/17.6 | KOH 0.21 g H₂O 8 ml | 0.5 kg/cm² (at −60° C.) | −60° C.-0° C., 15 min., 0° C., 2 hr. | 41.2 | 15.9 | 42.9 | Trace |
| 5 | " | " | 0.6 kg/cm² (at −60° C.) | −60° C.-0° C., 15 min., 0° C., 2 hr. | 36.4 | 14.4 | 49.2 | " |
| 6 | " | " | 1.0 kg/cm² (at −60° C.) | −60° C.-0° C., 15 min., 0° C., 2 hr. | 22.7 | 8.0 | 69.3 | " |
| 7 | 40.0/60.0 | " | 1.0 kg/cm² (at −60° C.) | −60° C.-0° C., 15 min. 0° C., 15 min. | 50.8 | 8.6 | 39.7 | 0.9 |

Note:
(III) 4-Isopropenyl-3,7-dimethyl-6-octen-1-yn-3-ol
(IV) 3-Isopropenyl-6-methyl-5-hepten-2-one
(V) 3-Isopropylidene-6-methyl-5-hepten-2-one

Example 8

The reaction procedure described in Example 1, Section 1, under the title of "Production of the α,β- and β,γ-unsaturated ketones" was repeated except that 590 g of 2,3-dimethyl-1-chloro-2-butene was used in lieu of 520 g of prenyl chloride producing 730 g of a mixture of 3-isopropenyl-5,6-dimethyl-5-hepten-2-one and 3-isopropylidene-5,6-dimethyl-5-hepten-2-one in a 6:1 ratio as a high-boiling distillate (bp. 92.0°–95.5° C./5.5 mm Hg). The products have a structural formulas:

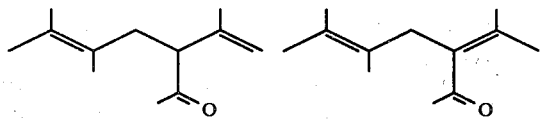

The structural identification of the products were determined in the following manner:
Infrared absorption spectrum (cm⁻¹):
3070, 1712, 1640, 1445, 1373, 1350, 1152, 898
Nuclear magnetic resonance spectrum (δinCCl₄ppm):

| | |
|---|---|
| 1.51, 1.54, 1.57, 1.58 | (s, 12H, CH₃—) |
| 1.93 | (s, 3H, CH₃C—) ‖ O |
| 1.88–2.55 3.13 | (m, 2H, —CH₂—) |
| | (t, 1H, —C—CH—) ‖ O |
| 4.73 | (s, 2H, ═CH₂) |

Into an autoclave with a capacity of 5 liters were placed 2500 ml of liquid ammonia and 56 g of the unsaturated ketone mixture obtained by the above reaction. A 20 weight percent aqueous solution of 2.8 g of potassium hydroxide as a catalyst and acetylene gas was then passed into the mixture at −60° C. to provide a total pressure of about 1.5 kg/cm². The reaction temperature was increased to 5° C. (increasing the total pressure to 14.5 kg/cm²) the temperature was maintained for 4 hours. The reaction temperature was then lowered to −40° C. and the reaction mixture was neutralized with ammonium chloride. Following removal of the ammonia, the residue was poured in water and extracted with ether. The extract was dried over anhydrous sodium sulfate and the solvent was distilled off under reduced pressure. The residue was further distilled under reduced pressure to obtain 58.5 g of a distillate boiling at 89°–92° C./2.3 mm Hg. Gas chromatographic analysis of this distillate showed that it was a mixture of 3-isopropenyl-5,6-dimethyl-5-hepten-2-one (3.5%), 3-isopropylidene-5,6-dimethyl-5-hepten-2-one (12.5%) and principally, 4-isopropenyl-3,6,7-trimethyl-1-octyn-6-en-3-ol (84%) having the formula:

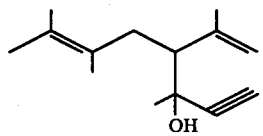

The structural identification of the principal product was accomplished by the following methods:
Infrared absorption spectrum (cm⁻¹):
3440, 3300, 3070, 1639, 1450, 1375, 900
Nuclear magnetic resonance spectrum (δinCCl₄ppm):

| 1.41 | (s, 3H, CH₃—C—O—) |
| 1.56 | (s, 9H, CH₃—) |
| 1.74 | (s, 3H, CH₃—) |
| 2.21–2.45 | (m, 3H, —CH₂—CH—) |
| 2.31 | (s, 1H, —C≡CH) |
| 4.86 | (s, 2H, —C=CH₂) |

EXAMPLE 9

1. Production of the α,β- and α,γ-unsaturated ketones

By a procedure similar to that described in Example 1, 142.8 g of geranyl chloride and 162.7 g of mesityl oxide were reacted in a solution of 99.6 g of sodium hydroxide in 81.5 g of water and in the presence of 5 g of methyltricyclohexylphosphonium chloride at 40° C. for 4 hours. The reaction mixture was poured into a container of water and the resulting aqueous solution was extracted with ether. The ethereal solution was washed with water and dried. The solvent and the unreacted mesityl oxide were distilled off under reduced pressure from the ethereal solution. The residue (188 g) was distilled in vacuo to obtain 164 g of a mixture (79.87% yield) of 3-isopropenyl-6,10-dimethyl-5,9-undecadien-2-one (58%) and 3-isopropylidene-6,10-dimethyl-5,9-undecadien-2-one (42%) as a distillate boiling at 80°–98° C./0.2 mm Hg. This mixture was rectified to obtain 76 g of 3-isopropenyl-6,10-dimethyl-5,9-undecadien-2-one (bp. 84°–89° C./0.25 mm Hg) and 47 g of 3-isopropylidene-6,10-dimethyl-5,9-undecadien-2-one (bp. 93°–97° C./0.25 mm Hg), and 34 g of a middle distillate was also recovered. The major product has the formula:

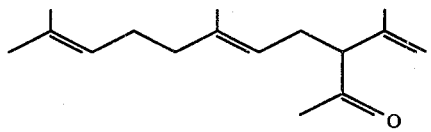

The structural identity of each product was established by the following methods:
Infrared absorption spectrum (cm⁻¹):
1713 (>C=O), 1670, 1640, (>C=C<), 1440, 1376, 1352, 1153, 1100, 900
Nuclear magnetic resonance spectrum (δinCCl₄ppm):

| 1.53, 1.57, 1.60 | (each s, 12H, CH₃—) |
| ca 1.92–2.05 | (m, 4H, —CH₂CH₂—) |
| 1.95 | (s, 3H, CH₃C—‖O) |
| ca 2.05–2.40 | (m, 2H, —CH₂—) |
| 3.05 | (t, 1H, —CH—) |
| 4.85, 4.87 | (each s, 2H, =CH₂) |
| 5.00 | (t, 2H, =CH—) |

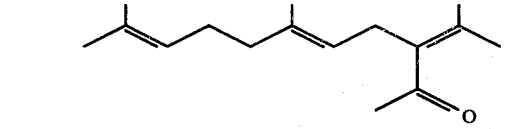

Infrared absorption spectrum (cm⁻¹):
1685 (>C=O), 1615, (>C=C<), 1440, 1375, 1351, 1200, 1170, 978, 850, 830
Nuclear magnetic resonance spectrum (δinCCl₄ppm):

| 1.53, 1.58 | (each s, 9H, CH₃—) |
| 1.69, 1.75 | (each s, 6H, CH₃—) |
| ca 1.95–2.10 | (m, 4H, —CH₂CH₂—) |
| 2.04 | (s, 3H, CH₃C—‖O) |
| 2.89 | (d, 2H, —CH₂—) |
| 4.99 | (t, 2H, =CH—) |

2. Isomerization of the α,β-unsaturated ketones

The above middle distillate (34 g) and 3-isopropylidene-6,10-dimethyl-5,9-undecadien-2-one (47 g) and 5 g of 4-nitroisophthalic acid were heated to effect distillation and isomerization in a rectifying column with 50 theoretical plates at a reduced pressure of 5 mm Hg with a reflex ratio of 30:1 yielding 64 g of distillate. Gas chromatographic analysis of this distillate revealed that it was a mixture of 3-isopropenyl-6,10-dimethyl-5,9-undecadien-2-one (92 weight percent) and 3-isopropylidene-6,10-dimethyl-5,9-undecadien-2-one (8 weight percent).

3. Production of the substituted propargyl alcohol

The above distillate mixture was combined with 76 g of 3-isopropenyl-6,10-dimethyl-5,9-undecadien-2-one and was placed into a 2 liter three-necked flask with 1 liter of liquid ammonia, followed by the addition of 13 g of sodium metal. Acetylene gas was bubbled through the resultant reaction mixture. When the reaction mixture turned a grey color, 140 g of 3-isopropenyl-6,10-dimethyl-5,9-undecadien-2-one were added. The introduction of acetylene gas was continued at −33° C. for 3 hours to effect the ethynylation reaction. Upon completion of the reaction, the ammonia was removed. The reaction mixture was then neutralized by the addition of ammonium chloride, poured into a container of water and the resulting aqueous solution was extracted with ether. The ethereal layer was dried over anhydrous sodium sulfate and the solvent was distilled off under reduced pressure. The residue was distilled under high vacuum to obtain 138 g of 4-isopropenyl-3,7,11-trimethyldodeca-6,10-dien-1-yn-3-ol as a distillate boiling at 120°–125° C./0.3 mm Hg. Gas chromatographic analysis of this distillate showed that it contained 1 weight percent of 3-isopropenyl-6,10-dimethyl-5,9-undecadien-2-one and 4 weight percent of 3-isopropylidene-6,10-dimethyl-5,9-undecadien-2-one. The product had the following structural formula:

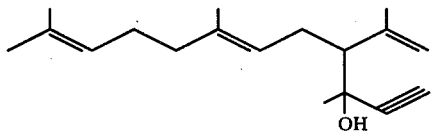

The structural identity of the product was established by the following methods:

Infrared absorption spectrum (cm$^{-1}$):
3500, 3450(-OH), 3290, 1630, 1442, 1373, 1125, 1025, 942, 920, 895

Nuclear magnetic resonance spectrum ($\delta$inCCl$_4$ppm):

| | |
|---|---|
| 1.40 | (s, 3H, CH$_3$—) |
| 1.53, 1.58, 1.75 | (s, 12H, CH$_3$—) |
| ca 1.87–2.50 | (m, 7H, —CH$_2$CH$_2$—, —CH$_2$—CH—) |
| 2.30 | (s, 1H, —C≡CH) |
| ca 4.70–5.15 | (m, 4H, =CH$_2$, =CH—) |

4. Production of the allylic alcohol 47.2 g of 4-isopropenyl-3,7,11-trimethyldodeca-6,10-dien-1-yn-3-ol was dissolved in 500 ml of n-hexane in contact with 4.7 g of 0.25% Lindlar catalyst and partially hydrogenated under atmospheric pressure and at room temperature. The partial hydrogenation was sequentially monitored by gas chromatography (PEG 20 M) and terminated after all the starting material had reacted. The reaction mixture was then filtered to recover the catalyst and the filtrate was distilled under reduced pressure to remove the solvent, yielding 45.8 g of residue. The residue was analyzed by gas chromatography, infrared absorption spectroscopy, mass spectroscopy and nuclear magnetic resonance spectroscopy. It was found that the above residue was 4-isopropenyl-3,7,11-trimethyldodeca-1,6,10-trien-3-ol of the formula:

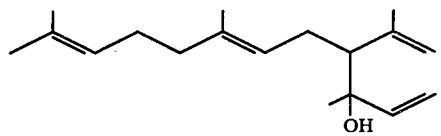

This product boiled at 105°–109° C./0.09 mm Hg.

5. Production of the δ,ε-unsaturated ketone

Into a 100 ml three-necked flask 40 g 4-isopropenyl-3,7,11-trimethyldodeca-1,6,10-trien-3-ol was placed and, in a nitrogen atmosphere heated to 185°–190° C. for 3 hours and rearranged. The reaction mixture was directly distilled in vacuo to remove, as a low-boiling fraction, 2,6,10-trimethyl-2,5,9-undecatriene, which was a decomposition product, and 3-isopropenyl-6,10-dimethyl-5,9-undecadien-2-one and 3-isopropylidene-6,10-dimethyl-5,9-undecadien-2-one which had been contained as impurities in the starting allylic alcohol. A higher-boiling fraction yielded 26.8 g 6,10,14-trimethyl-6,9,13-pentadecatrien-2-one. The rearrangement product had a structural formula:

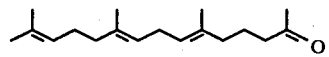

This product boiled at 120°–130° C./0.1 mm Hg. The structural identity of this product was established on the basis of its infrared absorption and nuclear magnetic resonance spectra.

Infrared absorption spectrum (neat):
1715, 1672, 1440, 1158, 1170 (cm$^{-1}$)

Nuclear magnetic resonance spectrum ($\delta$inCCl$_4$ppm):

| | |
|---|---|
| 1.57, 1.60, 1.63 | (each s, 12H, CH$_3$—) |
| ca 1.70–2.50 | (m, 10H, —CH$_2$—) |
| 2.00 | (s, 3H, CH$_3$C—) ‖ O |
| 2.67 | (d, 2H, —CH$_2$—) |
| 5.06 | (broad t, 3H, =CH—) |

This unsaturated ketone was converted to phytone by hydrogenation in contact with palladium-on-carbon and, then, reacted with a vinyl-Grignard reagent. The resultant product gave the same results when compared with a commercial sample of isophytol in gas chromatographic retention time and nuclear magnetic resonance spectrum data.

EXAMPLE 10

The reaction procedure described in Example 9, Section 1, under the title of "Production of the α,β- and β,γ-unsaturated ketones" was repeated except that isomesityl oxide of 98.4% purity was used in lieu of mesityl oxide. By this procedure was obtained 164 g of a mixture of 3-isopropenyl-6,10-dimethyl-5,9-undecadien-2-one (58 weight percent) and 3-isopropylidene-6,10-dimethyl-5,9-undecadien-2-one (42 weight percent) as a distillate boiling at 80°–98° C./0.2 mm Hg (yield 79.87%).

The above mixture was rectified by a procedure similar to that described in Example 9 and 76 g of the resultant 3-isopropenyl-6,10-dimethyl-5,9-undecadien-2-one was reacted in 1000 ml of liquid ammonia and in contact with a catalyst comprising 1.3 g of potassium hydroxide and 5 ml of water with acetylene gas being introduced to give a total pressure at $-5°$ C. of 6.7 kg/cm$^2$. The reaction was conducted in an autoclave at $-5°$ C. for 3 hours. Upon completion of the reaction, following the removal of ammonia, the reaction mixture was neutralized with ammonium chloride and the residue was poured into a container of water and the resulting aqueous solution was extracted with ether. The ethereal extract was dried over anhydrous sodium sulfate. First, the solvent was distilled off under reduced pressure and then the residue was distilled under reduced pressure to obtain 77.4 g of a distillate at bp. 120°–125° C./0.3 mm Hg. Gas chromatographic analysis of this distillate showed that it was a mixture of 3-isopropenyl-6,10-dimethyl-5,9-undecadien-2-one (3.6 weight percent), 3-isopropylidene-6,10-dimethyl-5,9-undecadien-2-one (12.3 weight percent) and 4-isopropenyl-3,7,11-trimethyldodeca-6,10-dien-1-yn-3-ol (84.1 weight percent).

Separately, 34 g of the mixture of 3-isopropenyl-6,10-dimethyl-5,9-undecadien-2-one and 3-isopropylidene-6,10-dimethyl-5,9-undecadien-2-one was reacted in 500 ml of liquid ammonia in contact with a catalyst comprising 0.62 g of potassium hydroxide in 2.3 ml of water, with acetylene gas which was introduced into the reaction mixture to give a total pressure at 5° C. of 10 kg/cm$^2$. The reaction was continued in an autoclave at 5° C. for 3 hours. Gas chromatographic analysis of the reaction mixture indicated a mixture of 3-isopropenyl-6,10-dimethyl-5,9-undecadien-2-one (5.2 weight percent), 3-isopropylidene-6,10-dimethyl-5,9-undecadien-2-one (15.7 weight percent) and 4-isopro-penyl-3,7,11-trimethyldodeca-6,10-dien-1-yn-3-ol (79.1 weight percent).

EXAMPLE 11

1. Production of the α,β- and β,γ-unsaturated ketones

A solution of 300 g (7.5 moles) of sodium hydroxide in 245 g of water, 522 g (5 moles) of prenyl chloride (purity 90%) and 980 g (10 moles) of mesityl oxide were stirred in contact with 24.2 g of trimethylstearylammonium chloride as a catalyst at a temperature of 32°–35° C. The reaction was sequentially monitored, the results are shown in Table II.

TABLE II

| Reaction time (hr.) | Conversion of prenylchloride (%) | 3-Isopropenyl isomer/3-isopropylidene isomer (Molar ratio) |
|---|---|---|
| 1.5 | 55 | 89.27/10.73 |
| 2.5 | 76 | 84.16/15.84 |
| 3.5 | 84 | 78.05/21.95 |
| 4.5 | 86 | 79.96/20.04 |
| 5.5 | 93 | 77.34/22.66 |

The reaction was completed in 5 hours and the product mixture was subjected to the after-treatments described in Example 1 to obtain 3-isopropenyl-6-methyl-5-hepten-2-one (yield 65%) and 3-isopropylidene-6-methyl-5-hepten-2-one (yield 12%). The 3-isopropylidene-6-methyl-5-hepten-2-one was isomerized and distilled by heating in contact with 5 g of indolebutyric acid yielding 76 g 3-isopropenyl-6-methyl-5-hepten-2-one (98% purity).

2. Production of the substituted propargyl alcohol

Into a 5 liter autoclave was placed 2 liters of liquid ammonia and 485 g of 3-isopropenyl-6-methyl-5-hepten-2-one and in contact with 2.5 g of potassium hydroxide, ethylation was carried out at $-2°$ to 5° C. by bubbling acetylene through the mixture. Upon completion of the reaction, the liquid ammonia was removed and the residue was poured into a container of water and the resulting aqueous solution extracted with ether. The ethereal extract was dried over anhydrous sodium sulfate and the solvent was removed. The residue was distilled under high vacuum to obtain 4-isopropenyl-3,7-dimethyl-6-octen-1-yn-3-ol in an overall yield of 70% based on prenyl chloride. The ethynylation product contained 2.0 weight percent of 3-isopropenyl-6-methyl-5-hepten-2-one and 13.0 weight percent of 3-isopropylidene-6-methyl-5-hepten-2-one.

3. Production of the allylic alcohol and δ,ε-unsaturated ketone

By a procedure similar to that described in Example 1, the above ethynylation product was partially hydrogenated in 2 liters of n-hexane and in contact with 30 g of 0.25% Lindlar catalyst at room temperatue and in atmospheric pressure. This method produced 4-isopropenyl-3,7-dimethyl-1,6-octadien-3-ol in a yield of 95%. This alcohol product was heated at 180° C. in a nitrogen atmosphere for 4 hours and the resultant mixture was distilled under reduced pressure to obtain 6,10-dimethyl-6,9-undecadien-2-one in a yield of 68%.

EXAMPLE 12

1. Production of α,β- and β,γ-unsaturated ketones

To 1 liter of liquid ammonia was added a small amount of ferric nitrate, followed by the addition of 23 g of sodium metal. The mixtue was stirred at $-40°$ C. for 1 hour to form sodium amide. Mesityl oxide (98 g) was added dropwise at a temperature between $-40°$ and $-33°$ C. to the sodium amide mixture; this temperature was maintained and the mixture was stirred for 30 minutes. To this mixture was added 152 g of isoamyl bromide. The ammonia was removed and replaced with 1 liter of diethyl ether. When the reaction temperature reached 0° C., the reaction mixture was neutralized with ammonium chloride and poured into a container of water. After washing with water, the ethereal layer was dried over anhydrous sodium sulfate. The solvent was distilled off under reduced pressure and the residue was distilled in vacuo, yielding 82 g of 3-isopropenyl-6-methylhepta-2-one as a distillate at bp. 72°–75° C./15–16 mm Hg. Gas chromatographic analysis determined that the product contained 13% of 3-isopropylidene-6-methylheptan-2-one.

2. Production of the substituted popargyl alcohol

In an autoclave, the above distillate was added to 1 liter of liquid ammonia in contact with 6 ml of 20% potassium methoxide as a catalyst at 0° C. for 6 hours, acetylene gas was bubbled through the mixture to produce a total pressure of 8 kg/cm$^2$. The reaction mixture was then neutralized and the ammonia was removed. The residue was poured into a container of water and the resulting aqueous solution was extracted with ether. The ethereal layer was washed with water and dried. The ethereal extract was then concentrated under reduced pressure to remove the solvent and the residue was distilled to obtain 81.5 g of 4-isopropenyl-3,7-dimethyl-1-octyn-3-ol as a distillate at bp. 66°–66.5° C./1.5 mm Hg. Gas chromatographic analysis of this distillate confirmed a mixture of 3-isopropenyl-6-methylheptan-2-one (6.6 weight percent), 3-isopropylidene-6-methylheptan-2-one (15.7 weight percent) and 4-isopropenyl-3,7-dimethyl-1-octyn-3-ol (77.7 weight percent). The last named compound had a structural formula:

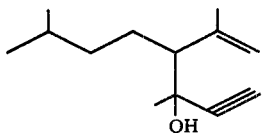

The structural identification of the product was determined by the following methods:

Infrared absorption spectrum (cm$^{-1}$): 3460, 3300, 1638, 1469, 1451, 1040, 1009, 922, 896

Nuclear magnetic resonance spectrum ($\delta$inCCl$_4$ppm):

| | |
|---|---|
| 0.80, 0.91 | (s, 6H, CH$_3$—) |
| 1.40 | (s, 3H, CH$_3$—) |
| 1.73, 1.75 | (s, 3H, CH$_3$—) |
| ca 1.10–2.25 | (m, 6H, —CHCH$_2$CH$_2$CH—) |
| 2.27 | (s, 1H, —C≡CH) |
| ca 4.84, 4.95 | (each broad s, 2H, —C=CH$_2$) |

EXAMPLE 13

1. Production of the $\alpha,\beta$- and $\beta,\gamma$-unsaturated ketones

Sodium metal (23 g) was mixed with liquid ammonia (500 ml) and reacted by contacting the resulting solution with a catalytic amount of ferric chloride to produce sodium amide. A mixture of 176 g of tetrahydrogeranyl chloride and 196 g of mesityl oxide were added dropwise to the sodium amide mixture and the resulting mixture was stirred at −33° C. for 2 hours. Upon completion of the reaction, the ammonia was removed from the reaction mixture and the residue was neutralized with ammonium chloride, poured into a container of water and the resulting aqueous solution was extracted with ether. The extract was dried over anhydrous sodium sulfate, and the solvent and the unreacted mesityl oxide were distilled off under reduced pressure. The residue was vacuum distilled to obtain 178.5 g of 3-isopropenyl-6,10-dimethylundeca-2-one (yield 75%) as a distillate at bp. 95°–98° C./0.50 mm Hg. Gas chromatographic analysis of this distillate determined 11% of 3-isopropylidene-6,10-dimethylundeca-2-one.

2. Production of the substituted propargyl alcohol

The ethynylation of 178.5 g of 3-isopropenyl-6,10-dimethylundeca-2-one was conducted in a 2 liter autoclave in 700 ml of N-methylpyrrolidone and in contact with 2 g of potassium hydroxide. The reaction temperature 0°–5° C. was maintained for 3 hours. The reaction mixture was poured into a container of water and the resulting aqueous solution was extracted with ether. The ethereal layer was washed with water, dried and distilled under reduced pressure to remove the solvent. The residue was distilled under high vacuum to yield 173 g of 4-isopropenyl-3,7,11-trimethyldodeca-1-yn-3-ol as a distillate at bp. 110°–115° C./0.2 mm Hg. Gas chromatographic analysis of this distillate indicated 12.4 weight percent of 3-isopropylidene-6,10-dimethylundeca-2-one and 2.0 weight percent of 3-isopropenyl-6,10-dimethylundeca-2-one.

3. Production of the allylic alcohol and the $\delta,\epsilon$-unsaturated ketone The substituted propargyl alcohol produced above was partially hydrogenated in a 1 liter autoclave containing 500 ml of n-heptane and in contact with 5 g of 0.25% Lindlar catalyst at an elevated pressure (40 kg/cm$^2$). Upon completion of the hydrogenation, the reaction mixture was distilled to obtain 165 g of 4-isopropenyl-3,7,11-trimethyldodeca-1-en-3-ol as a distillate at bp. 107°–112° C./0.1 mm Hg. This product was heated at 180°–185° C. for 5 hours and yielded 6,10,14-trimethylpentadeca-6-en-2-one in a yield of 64%.

EXAMPLES 14–19

The condensation reaction of different organic halides (R-halo) with mesityl oxide under varying conditions produced $\alpha,\beta$-unsaturated ketones (V) and $\beta,\gamma$-unsaturated ketones (IV). Each of the separated $\beta,\gamma$-unsaturated ketones (IV) were ethynylated and the resultant propargyl alcohol (III) was subjected to partial hydrogenation in the presence of the Lindlar catalyst. The resultant allylic alcohol (II) was heated to obtain $\delta,\epsilon$-unsaturated ketone (I) as a rearrangement product. The results are summarized in Table III, Table IV and Table V.

TABLE III

| | Reaction of the Organic Halide with Mesityl Oxide | | | | | |
|---|---|---|---|---|---|---|
| EXAMPLE | Organic halide R-halo | | Mesityl oxide (mol.) | Reaction conditions | Yield (%) of the formed ketones (IV) +(V) | Mole ratio, (IV)/(V) |
| | Type | Amount (mol.) | | | | |
| 14 | ![structure]Br | 2.0 | 4.0 | Sodium (2.0 mol.) in ammonia, Ferric chloride catalyst −33°, 6 hrs. | 80 | 89/11 |
| 15 | ![structure]Cl | 1.0 | 1.8 | Sodium (1.1 mol.) in ammonia, Ferric chloride catalyst −33° C., 6 hrs. | 80 | 90/10 |

TABLE III-continued
Reaction of the Organic Halide with Mesityl Oxide

| EXAMPLE | Organic halide R-halo Type | Amount (mol.) | Mesityl oxide (mol.) | Reaction conditions | Yield (%) of the formed ketones (IV)+(V) | Mole ratio, (IV)/(V) |
|---|---|---|---|---|---|---|
| 16 | [structure with Br] | 2.0 | 4.0 | 55% aqueous solution of NaOH (3 mol.), Trimethyl-stearyl-ammonium chloride, 35° C. 2 hrs. | 86 | 75/25 |
| 17 | [structure with Cl] | 1.0 | 3.0 | 55% aqueous solution of NaOH (2.0 mol.), Trimethyl-stearyl-ammonium chloride, 35°–45° C., 3 hrs. | 83 | 73/27 |
| 18 | [structure with Br] | 1.0 | 2.5 | 55% aqueous solution of KOH (2.0 mol.), Trimethyl-stearyl-ammonium chloride, 40° C. 2 hrs. | 84 | 77/23 |
| 19 | [structure with OH and Br] | 1.0 | 4.0 | Sodium (1.0 mol.) in ammonia, Ferric chloride catalyst −33° C., 3 hrs. | 72 | 91/9 |

TABLE IV

| EXAMPLE | Ethynylation Reaction of the β,γ-Unsaturated Ketone (IV) Reaction Conditions | Formed propargyl alcohol (III) Type | Yield (%) based on (IV) | Partial Hydrogenation of (III) Yield (%) of the formed allylic alcohol (II) based on (III) |
|---|---|---|---|---|
| 14 | Sodium (1.4 mol.) in ammonia, Released system | [structure] | 87 | 82 |
| 15 | Sodium (0.7 mol.) in ammonia, Released system | [structure] | 86 | 81 |
| 16 | KOH (1 weight %) in ammonia at 0°–5° C. for 5 hrs. in autoclave | [structure] | 95 | 90 |
| 17 | KOH (1 weight %) in N-methyl-pyrrolidone at 0°–3° C. for 5 hrs. in autoclave | [structure] | 95 | 91 |
| 18 | KNH₂ (0.5 weight %) in ammonia at 3°–6° C. for 5 hrs. in autoclave | [structure] | 94 | 87 |
| 19 | KOH (1 weight %) in dimethylformamide at −2°–+3° C. for 5 hrs. in autoclave | [structure] | 94 | 88 |

TABLE V

Rearrangement Reaction of the Allylic Alcohol (II)

| EXAMPLE | Reaction Conditions | Formed δ,ε-unsaturated ketone (I) Type | Yield (%) based on (II) |
|---|---|---|---|
| 14 | 180°–185° C., 4 hrs. | (structure) | 63 |
| 15 | 180°–185° C., 5 hrs. | (structure) | 67 |
| 16 | 185°–190° C., 3 hrs. | (structure) | 65 |
| 17 | 185°–190° C., 3 hrs. | (structure) | 66 |
| 18 | 185°–190° C., 3 hrs. | (structure) | 65 |
| 19 | 150°–155° C., 10 hrs. | (structure) | 57 |

EXAMPLES 20–24

Suitable organic halides (R-halo) were condensed with mesityl oxide under varying conditions to prepare α,β-unsaturated ketones (V) and β,γ-unsaturated ketones (IV). Each of the β,γ-unsaturated ketones (IV) was ethynylated to produce the corresponding substituted propargyl alcohol (III). The results are shown in Table VI.

TABLE VI

Reaction of the organic halide with mesityloxide

| EXAMPLE | Organic halide R-halo. Type | Amount (mol) | Mesityl oxide (mol) | Reaction conditions | Yield (%) of the formed ketones, (IV)+(V) | Mole ratio, (IV)/(V) |
|---|---|---|---|---|---|---|
| 20 | (structure) | 2.0 | 2.0 | Sodium (2.0 mol.) in ammonia, Ferric chloride catalyst, −33° C., 6 hrs. | 62 | 88/12 |
| 21 | (structure) | 1.0 | 1.0 | Sodium (1.1 mol.) in ammonia, Ferric chloride catalyst, −33° C., 6 hrs. | 58 | 90/10 |
| 22 | (structure) | 2.0 | 2.0 | Sodium (2.0 mol.) in ammonia, Ferric chloride catalyst, −33° C., 6 hrs. | 65 | 89/11 |
| 23 | (structure) | 1.0 | 2.5 | 55% aqueous solution of NaOH(2.0 mol.), Trimethylstearylammonium chloride, 35°–40° C., 3 hrs. | 80 | 75/25 |
| 24 | (structure) | 1.0 | 3.0 | 55% aqueous solution of KOH(2.0 mol.), Trimethylstearylammonium chloride, 40° C., 2 hrs. | 81 | 78/22 |

Ethynylation reaction of the β,γ-unsaturated ketone (IV)

| EXAMPLE | Reaction conditions | Formed propargyl alcohol (III) Type | Yield (%) based on (IV) |
|---|---|---|---|
| 20 | Sodium (1.4 mol.) in ammonia, Released system | (structure) | 91 |
| 21 | Sodium (0.7 mol.) in ammonia, Released system | (structure) | 85 |
| 22 | Sodium (1.4 mol.) in ammonia, Released system | (structure) | 93 |

TABLE VI-continued

| | | | |
|---|---|---|---|
| 23 | KOH (1 wt. %) in N-methylpyrrolidone at 0°–3° C. for 5 hrs. in autoclave | | 91 |
| 24 | KNH$_2$ (0.5 wt. %) in ammonia at 3.6° C. for 5 hrs. in autoclave | | 92 |

EXAMPLE 25

1. Production of the δ,ε-unsaturated ketone

A solution of 98.1 g of 4-isopropenyl-3,7-dimethyl-1,6-octadien-3-ol in N-methylpyrrolidone was purged with nitrogen gas, and the solution was reacted with stirring at 180° C. for 4 hours. The reaction mixture was poured into a container of water and the resulting aqueous solution was extracted with ether. The ethereal layer was washed with water, dried over anhydrous sodium sulfate and concentrated under reduced pressure to remove the solvent. The residue was distilled in vacuo to obtain 76.5 g of a distillate boiling at 77°–82° C./0.15 mm Hg. Gas chromatographic analysis of this distillate revealed that the product was 6,10-dimethyl-6,9-undecadien-2-one, and the starting material 4-isopropenyl-3,7-dimethyl-1,6-octadien-3-ol was substantially completely reacted.

2. Ethynylation of the δ,ε-unsaturated ketone

The 6,10-dimethyl-6,9-undecadien-2-one obtained as above was ethynylated in liquid ammonia to form 3,7,11-trimethyl-7,10-dodecadien-1-yn-3-ol (bp. 108°–115° C./0.5 mm Hg). The compound had the structural formula:

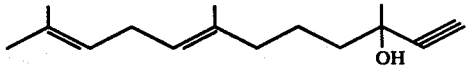

The structure of this product was identified by the following methods:
Infrared absorption spectrum (cm$^{-1}$):
3400, 3300, 2120, 1660, 1450, 1376, 1120, 920, 650, 630
Nuclear magnetic resonance spectrum (δinCCl$_4$ppm):

| | |
|---|---|
| 1.39 | (s, 3H CH$_3$—) |
| 1.57 | (broad s, 9H, CH$_3$—) |
| ca 1.70–2.20 | (m, 6H, —CH$_2$CH$_2$CH$_2$—) |
| 2.27 | (s, 1H, —C≡CH) |
| ca 2.40–2.75 | (m, 2H, —C=CH$_2$—C—) |
| ca 4.95–5.20 | |
| | (m, 2H, —C=CH—) |

3. Production of squalene

In contact with triphenylphosphine rhodium chloride [RhCl (PPh$_3$)$_3$] catalyst, 3,7,11-trimethyl-7,10-dodecadien-1-yn-3-ol was refluxed in benzene for 3 hours. The reaction mixture was concentrated and purified by column chromatography (developer system: benzene-chloroform=1:1). Analysis of the product by gel permeation chromatography showed that the starting material had substantially reacted to yield 2,6,10,15,19,23-hexamethyl-2,6,11,18,22-tetracosapenta-en-13-yn-10,15-diol (94% selectivity). The resulting acetylenic diol was hydrogenated in n-hexane and in contact with 5% palladium-on-carbon at room temperature and elevated pressure of 80–100 kg/cm$^2$ to yield 2,6,10,15,19,23-hexamethyltetracosa-10,15-diol (bp. 218°–220° C./0.2 mm Hg). This product was subjected to hydrogenolysis in acetic acid in contact with palladium-on-carbon at a hydrogen pressure of 100 kg/cm$^2$ and at a reaction temperature of 170°–190° C. The resultant compound was analyzed by gas chromatography and nuclear magnetic resonance spectroscopy and the data conformed with a standard sample of squalene.

EXAMPLE 26

The rearrangement of 4-isopropenyl-3,7-dimethyl-1,6-octadien-3-ol was carried out in various solvents which have the suitable proton exchange times as defined hereinbefore.

The rearrangement reactions were carried out in the following manner: three (3) grams of the allylic alcohol mentioned above were mixed with 1.5 g and 3.0 g of each solvent and each of the mixtures were heated at 170° C. for 2 hours. The reaction mixture was analyzed by gas chromatography. The selectivity for product 6,10-dimethyl-6,9-undecadien-2-one is shown in Table VII. Since the selectivity value for this rearrangement reaction is not significantly influenced by the conversion of allylic alcohol under the above conditions, the selectivity value stands for the product yield.

TABLE VII

| | Proton exchange time $t_o$ (sec.) | | Selectivity (%) Amount of the solvent | |
|---|---|---|---|---|
| Solvent | at 30° C. | at 100° C. | 1.5 g | 3.0 |
| 2-Pyrrolidone | 3.6 × 10$^{-1}$ | 8.8 × 10$^{-2}$ | 74.6 | 77.6 |
| N-methyl-2-pyrrolidone | Not less than 4.0 × 10$^{-1}$ | 1.8 × 10$^{-1}$ | 75.2 | 79.3 |
| ε-Caprolactam | Not less than 4.0 × 10$^{-1}$ | 1.9 × 10$^{-1}$ | 74.2 | 78.1 |
| N-(3-butanon-1-yl)-ε-captolactam | Not less than 4.0 × 10$^{-1}$ | 1.8 × 10$^{-1}$ | 73.8 | 79.2 |
| 2-Hydroxypyridine | 2.0 × 10$^{-1}$ | 1.6 × 10$^{-2}$ | 72.4 | 74.5 |
| 3-Hydroxypyridine | 1.8 × 10$^{-1}$ | 3.8 × 10$^{-2}$ | 69.8 | 73.3 |
| N,N-dimethylformamide | 1.3 × 10$^{-1}$ | 5.6 × 10$^{-2}$ | 79.6 | 76.1 |
| N-acetylaniline | 2.4 × 10$^{-1}$ | 1.3 × 10$^{-2}$ | 61.5 | 62.4 |
| Ethylene urea | 3.6 × 10$^{-1}$ | 2.0 × 10$^{-1}$ | 62.3 | 72.0 |
| Diphenyl urea | 7.6 × 10$^{-1}$ | 2.6 × 10$^{-2}$ | 74.0 | 73.6 |
| Triphenyl amine | 1.3 × 10$^{-1}$ | 2.4 × 10$^{-2}$ | 62.1 | 63.4 |
| Benzimidazole | 1.9 × 10$^{-1}$ | 7.4 × 10$^{-2}$ | 66.9 | 70.0 |

TABLE VII-continued

| Solvent | Proton exchange time $\zeta_o$ (sec.) at 30° C. | at 100° C. | Selectivity (%) Amount of the solvent 1.5 g | 3.0 |
|---|---|---|---|---|
| None | — | — | (59) | |
| Benztriazole | $1.3 \times 10^{-2}$ | Not more than $7.0 \times 10^{-3}$ | 49.3 | 12.2 |
| Dimethylsulfoxide | $1.7 \times 10^{-3}$ | $4.8 \times 10^{-4}$ | 30.7 | 31.3 |

EXAMPLE 27

In a nitrogen atmosphere, a mixture of 500 g of 4-isopropenyl-3,7,11-trimethyl-1,6-10-dodecatrien-3-ol (purity 89.61%) and 500 g of N-methylpyrrolidone was heated at 190° C. for 4 hours. The reaction mixture was cooled, poured into a container of water and the resulting aqueous solution was extracted with ether. The ethereal layer was washed with a saturated aqueous solution of sodium chloride and dried over anhydrous sodium sulfate. The ethereal extract was distilled under reduced pressure to remove the ether and low-boiling fractions, and the residue was distilled in vacuo to obtain 6,10,14-trimethyl-6,9,13-pentadecatrien-2-one (yield 73%) as a distillate at bp. 121°–123° C./0.17 mm Hg.

6,10,14-trimethyl-6,9,13-pentadecatrien-2-one is shown in Table VIII.

TABLE VIII

| Solvent | Proton exchange time $\zeta_o$ (sec.) at 30° C. | at 100° C. | Selectivity (%) Amount of the solvent 1.5 g | 3.0 g |
|---|---|---|---|---|
| 2-Hrydroxypyridine | $1.81 \times 10^{-1}$ | $3.6 \times 10^{-2}$ | 70.8 | 81.3 |
| 3-Hydroxypyridine | $2.30 \times 10^{-1}$ | $8.8 \times 10^{-2}$ | 71.6 | 79.9 |
| None | — | — | 66 | |

EXAMPLES 29-32

In 150 ml of liquid ammonia and in contact with a catalyst consisting of 0.21 g of potassium hydroxide in 0.8 ml of water, 12.45 g of a mixture of 3-isopropenyl-6,10-dimethyl-5,9-undecadien-2-one (58%) and 3-isopropylidene-6,10-dimethyl-5,9-undecadien-2-one (42%) prepared in the same manner as in Example 9, was ethynylated in an autoclave. Upon completion of the reaction, the mixture was neutralized with ammonium chloride and the liquid ammonia was removed. The residue was dissolved in ether and poured into a container of water, followed by extraction with ether. The ethereal layer was washed with water, dried and distilled under reduced pressure to remove the ether. The residue was analyzed by gas chromatography. The results are disclosed in Table IX.

TABLE IX

| EXAMPLE | Ethynylation Total pressure (ammonia plus acetylene) | Reaction conditions | Composition of the reaction mixture Ketones (wt. %) 3-isopropenyl 1 | 3-isopropylidene 2 | Ethynylation product (wt. %) 3 |
|---|---|---|---|---|---|
| 29 | 3.7 kg/cm² at −30°–−10° C. 5.5 kg/cm² at 0° C. 9.2 kg/cm² at 15° C. | 1 hr. at −30°–+16° C. and 6 hrs. at 16° C. | 6.30 | 22.55 | 71.15 |
| 30 | 4.0 kg/cm² at −30°–−10° C. 7.7 kg/cm² at 5° C. | 1 hr. at −30°–+5° C. and 3 hrs. at 5° C. | 5.20 | 15.73 | 79.07 |
| 31 | 12.5 kg/cm² at −30°–−10° C. 11.6 kg/cm² at 0° C. | 0.5 hr. at −45°–0° C. and 3 hrs. at 0° C. | 7.65 | 15.14 | 77.22 |
| 32 | 5.2 kg/cm² at −30°–−11° C. 6.7 kg/cm² at −5° C. | 10 min. at −40°–−5° C. and 3 hrs. at −5° C. | 4.48 | 14.69 | 80.84 |

1 3-isopropenyl-6,10-dimethyl-5,9-undecadien-2-one
2 3-isopropyliden-6,10-dimethyl-5,9-undecadien-2-one
3 4-isopropenyl-3,7,11-trimethyldodeca-6,10-dien-1-yn-3-ol

EXAMPLE 28

To 3 g of 4-isopropenyl-3,7,11-trimethyl-1,6,10-dodecatrien-3-ol were added 1.5 g or 3 g of the nitrogen-containing solvents shown in Table VIII. The resultant mixture was heated at 180° C. in a nitrogen atmosphere for 3 hours. The selectivity for the product

EXAMPLES 33-45

Isomerization of the α,β-unsaturated ketone

The α,β-unsaturated ketone, 3-isopropyliden-6-methyl-5-hepten-2-one (purity 97.1%) was isomerized to obtain 3-isopropenyl-6-methyl-5-hepten-2-one. The reaction conditions and the results are shown in Table X.

TABLE X

| | Base | | Catalyst | | Reaction conditions | | Results of Reaction | |
|---|---|---|---|---|---|---|---|---|
| EXAMPLE | Type | Amount (wt. %/ ketone) | Type | Amount (wt. %/ ketone) | Temperature (°C.) | Time (min.) | Molar Ratio 1 | Selectivity of reaction 2 |
| 33 | 55% NaOH aqueous solution | 257 | — | 0 | 70 | 60 | 0.13 | 96.3 |
| 34 | 55% NaOH aqueous solution | 332 | Trimethylstearyl-ammonium chloride | 1.03 | " | " | 0.49 | 97.2 |
| 35 | 25.3% NaOH aqueous solution | 195 | Trimethylstearyl-ammonium chloride | 0.95 | " | " | 0.42 | 95.5 |
| 36 | 40.3% NaOH aqueous solution | 240 | Trimethylstearyl-ammonium chloride | 0.90 | " | " | 0.51 | 96.3 |
| 37 | NaOH powder | 20 | — | 0 | " | 30 | 0.10 | 57.5 |
| 38 | 50% CH₃COONa aqueous solution | 100 | Ethyltricyclo-hexylphosphonium iodide | 1.0 | " | " | 0.10 | 57.5 |
| 39 | 20% KOH aqueous solutiom | 5 | (Liquid ammonia as reaction medium) | (600) | 0 | 60 | 0.35 | 99.0 |
| 40 | CH₃ONa powder | 20 | — | 0 | 70 | 30 | 0.11 | 43.8 |
| 41 | DBU | 5 | — | 0 | 70 | 60 | 0.21 | 98.1 |
| 42 | DBU | " | — | 0 | 120 | " | 0.47 | 95.3 |
| 43 | Triethanol amine | " | — | 0 | " | 120 | 0.03 | 91.2 |
| 44 | DABCO | " | — | 0 | " | 60 | 0.44 | 96.3 |
| 45 | Saturated MgCO₃ aqueous solution | 300 | Trimethylstearyl-ammonium chloride | 1.0 | 90 | 120 | 0.15 | 94.2 |

1 Molar ratio = [Amount of the resultant ketone (mole) in the reaction mixture] / [Amount of the starting ketone (mole) remaining in the reaction mixture]
2 Selectivity of the reaction = [Total amount of the starting ketone and resultant ketone after reaction] × 100 / [Amount of the charged starting ketone]

The following Reference Example A is included to show that the ethynylation of the unsaturated ketones (V) is difficult by conventional means. Reference Examples B and C show that 3-isopropylidene-6-methyl-5-hepten-2-one undergoes the isomerization reaction: α,β-unsaturated ketone (V)⇌β,γ-unsaturated ketone (IV) at a temperature particularly desirable for ethynylation under the pressure of acetylene (−15°—+15° C.). Reference Example D shows that mesityl oxide which is an α,β-unsaturated ketone having no substituent at α-position substantially does not undergo either an isomerization to β,γ-unsaturated ketone (isomesityl oxide) or an ethynylation reaction in the course of ethynylation at an elevated pressure of acetylene.

Reference Example A

Into a solution of 8.4 g of lithium metal dissolved in liquid ammonia, acetylene gas was bubbled to produce lithium acetylide. To the resulting solution of lithium acetylide was added 200 g of 3-isopropylidene-6-methyl-5-hepten-2-one and the introduction of acetylene gas was resumed. The reaction temperature was −33° C. and the reaction time was 4 hours. The reaction mixture was neutralized with ammonium chloride and, after the removal of the liquid ammonia, the residue was poured into a container of water and the resulting mixture was extracted with ether. Gas chromatographic analysis of the reaction mixture showed that, substantially, neither 3-isopropenyl-6-methyl-5-hepten-2-one nor 4-isopropenyl-3,7-dimethyl-6-octen-1-yn-3-ol had been produced.

Reference Example B

In a 500 ml autoclave, a mixture of 180 g of liquid ammonia, 52 g of 3-isopropylidene-6-methyl-5-hepten-2-one and, as a catalyst, a 20 weight percent aqueous solution of 1.15 g of potassium hydroxide were stirred at 0° C. The reaction mixture was sequentially sampled and analyzed by gas chromatography. The results disclosed that the ratios of 3-isopropenyl-6-methyl-5-hepten-2-one to 3-isopropylidene-6-methyl-5-hepten-2-one were 0.13 after 40 minutes, 0.24 after 1 hour, 0.33 after 1.5 hours, 0.39 after 2 hours and 0.40 after 4 hours.

Reference Example C

As in Reference Example B, a mixture of 180 g of liquid ammonia, 52 g of 3-isopropenyl-6-methyl-5-hepten-2-one and, a catalyst of 20 weight percent aqueous solution of 1.15 g of potassium hydroxide was stirred at 0° C. in an autoclave with a capacity of 500 ml. The reaction mixture was sequentially sampled and analyzed by gas chromatography. It was found that the ratios of 3-isopropenyl-6-methyl-5-hepten-2-one to 3-isopropylidene-6-methyl-5-hepten-2-one were 0.72 after 1 hour, 0.54 after 1.5 hours, 0.47 after 2 hours and 0.43 after 2.5 hours.

Reference Example D

Into a 300 ml autoclave were placed 150 ml of liquid ammonia, 7.4 g of mesityl oxide (containing 6% of isomesityl oxide) and, as a catalyst, a 20 weight percent aqueous solution of 0.21 g of potassium hydroxide. A acetylene gas was bubbled into the mixture to give a total pressure at −60° C. of 1 kg/cm². The reaction temperature was increased to 0° C. and the total pressure increased to 6.5 kg/cm². The mixture maintained at 0° C. was stirred for 6 hours. The reaction mixture was neutralized, the ammonia removed and the residue was poured into a container of water and the resulting aqueous solution was extracted with ether. The ethereal layer was washed with water and dried. The solvent was removed from the extract by distillation under reduced pressure and the residue was analyzed by gas chromatography. It was found that the reaction mixture was comprised almost exclusively of the starting material mesityl oxide, the ethynylation product being contained only in a very minor amount. The condensation product of mesityl oxide in a minor amount was also in evidence.

While the invention has now been described in terms of certain preferred embodiments and exemplified by way of comparative data, the skilled artisan will appreciate that various modifications, substitutions, omissions, and additions, may be made without departing from the spirit thereof. Accordingly, it is intended that the scope of the present invention be limited solely by that of the following claims.

What is claimed is:

1. An intermediate compound for the production of an unsaturated ketone via Oxy-Cope rearrangement reaction which comprises heating the corresponding allylic alcohol obtained by the hydrogenation of said compound to a temperature from 100° to 400° C., said compound being represented by the formula:

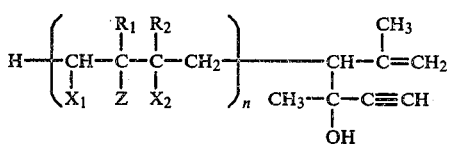

wherein $X_1$ and $X_2$ are both hydrogen atoms or wherein one of $X_1$ and $X_2$ is a hydrogen atom and the other jointly with Z represents a bond; Z jointly with $X_1$ or $X_2$ represents a bond, or separately represents a hydrogen atom; $R_1$ and $R_2$ are the same or different and represent hydrogen atoms or lower alkyl groups; n is 1 or 2; and when n is 2, $X_1$, $X_2$, Z, $R_1$, and $R_2$ may be the same or different.

2. An intermediate compound for the production of unsaturated ketone via Oxy-Cope rearrangement reaction which comprises heating said compound to a temperature from 100° to 400° C., said compound being represented by the formula:

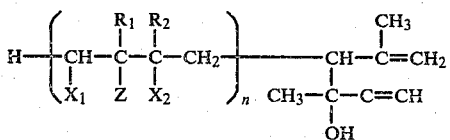

wherein $X_1$ and $X_2$ are both hydrogen atoms or wherein one of $X_1$ and $X_2$ is a hydrogen atom, the other jointly with Z represents a bond; Z jointly with $X_1$ or $X_2$ represents a bond or separately represents a hydrogen atom; $R_1$ and $R_2$ are the same or different and represent hydrogen atoms or lower alkyl groups; n is 1 or 2; and when n is 2, $X_1$, $X_2$, Z, $R_1$, and $R_2$ may be the same or different.

3. The compound according to claim 1 wherein $X_1$, $X_2$ and Z are hydrogen atoms.

4. The compound according to claim 1 wherein $X_1$, jointly with Z represents a bond and $X_2$ represents a hydrogen atom.

5. The compound according to claim 1 wherein $X_1$ is a hydrogen atom and $X_2$ jointly with Z represents a bond.

6. The compound according to claim 1 wherein one of $X_1$ or $X_2$ is a hydrogen atom and the other jointly with Z represents a bond; $R_1$ is methyl, $R_2$ is hydrogen, n is 1.

7. The compound according to claim 1 wherein one of $X_1$ and $X_2$ is a hydrogen atom and the other jointly with Z represents a bond; $R_1$ is methyl; $R_2$ is hydrogen; n is 2; $X_1$ and $X_2$ may be the same or different.

8. A compound according to claim 1, said compound being 4-isopropenyl-3,7-dimethyl-1-octyn-3-ol.

9. A compound according to claim 1 said compound being 4-isopropenyl-3,7-dimethyl-1-octyn-6-en-3-ol.

10. A compound according to claim 1, said compound being 4-isopropenyl-3,7-dimethyl-1-octyn-7-en-3-ol.

11. A compound according to claim 1, said compound being 4-isopropenyl-3,7,11-trimethyldodeca-1-yn-3-ol.

12. A compound according to claim 1, said compound being 4-isopropenyl-3,7,11-trimethyldodeca-1-yn-6,10-dien-3-ol.

13. A compound according to claim 1, said compound being 4-isopropenyl-3,7,11-trimethyldodeca-1-yn-10en-3-ol.

14. A compound according to claim 1, said compound being 4-isopropenyl-3,7,11-trimethyldodeca-1-yn-6-en-3-ol.

15. A compound according to claim 1, said compound being 4-isopropenyl-3,6,7-trimethyl-1-octyn-6-en-3-ol.

16. A compound according to claim 1, said compound being 4-isopropenyl-3,6,7-trimethyl-1-octyn-7-en-3-ol.

17. A compound according to claim 2 wherein $X_1$, $X_2$ and Z are hydrogen atoms.

18. A compound according to claim 2 wherein $X_1$ jointly with Z represents a bond and $X_2$ is a hydrogen atom.

19. A compound according to claim 2 wherein $X_1$ is a hydrogen atom and $X_2$ jointly with Z represents a bond.

20. A compound according to claim 2 wherein one of $X_1$ and $X_2$ is a hydrogen atom, the other jointly with Z represents a bond; $R_1$ is methyl, $R_2$ is hydrogen; and n is 1.

21. A compound according to claim 2 wherein one of $X_1$ and $X_2$ is a hydrogen atom, the other jointly with Z represents a bond; $R_1$ is methyl; $R_2$ is hydrogen; n is 2; and $X_1$ and $X_2$ may be the same or different.

22. A compound according to claim 2, said compound being 4-isopropenyl-3,7,-dimethyl-1-octen-3-ol.

23. A compound according to claim 2, said compound being 4-isopropenyl-3,7-dimethyl-1,6-octadien-3-ol.

24. A compound according to claim 2, said compound being 4-isopropenyl-3,7-dimethyl-1,7-octadien-3-ol.

25. A compound according to claim 2, said compound being 4-isopropenyl-3,7,11-trimethyldodeca-1-en-3-ol.

26. A compound according to claim 2, said compound being 4-isopropenyl-3,7,11-trimethyldodeca-1,6,10-trien-3-ol.

27. A compound according to claim 2, said compound being 4-isopropenyl-3,7,11-trimethyldodeca-1,10-dien-3-ol.

28. A compound according to claim 2, said compound being 4-isopropenyl-3,7,11-trimethyldodeca-1,6-dien-3-ol.

29. A compound according to claim 2, said compound being 4-isopropenyl-3,7,11-trimethyldodeca-1,6,11-trien-3-ol.

* * * * *